(12) United States Patent
Bron et al.

(10) Patent No.: US 7,553,637 B2
(45) Date of Patent: Jun. 30, 2009

(54) OXA1P ENHANCED PROTEIN SECRETION

(75) Inventors: Sierd Bron, Haren (NL); Harold Tjalsma, Groesbeek (NL); Jan M. Van Dijl, Harkstede (NL)

(73) Assignee: Danisco US Inc., Genencor Division, Palo Alto, CA (US)

( * ) Notice: Subject to any disclaimer, the term of this patent is extended or adjusted under 35 U.S.C. 154(b) by 149 days.

(21) Appl. No.: 10/500,660

(22) PCT Filed: Dec. 12, 2002

(86) PCT No.: PCT/US02/39634

§ 371 (c)(1),
(2), (4) Date: Mar. 31, 2005

(87) PCT Pub. No.: WO03/060068

PCT Pub. Date: Jul. 24, 2003

(65) Prior Publication Data

US 2005/0170511 A1 Aug. 4, 2005

(51) Int. Cl.
*C12N 15/00* (2006.01)
*C12N 15/75* (2006.01)
*C07H 21/04* (2006.01)

(52) U.S. Cl. ............... 435/69.1; 435/471; 536/23.1; 536/24.1

(58) Field of Classification Search .................. None
See application file for complete search history.

(56) References Cited

U.S. PATENT DOCUMENTS 5,824,502 A 10/1998 Honjo et al.
5,939,317 A 8/1999 Fayard et al.

OTHER PUBLICATIONS

The suplementary European search report mailed Feb. 14, 2006.
Tjalsma et al., "Complementary Impact of Paralogous Oxa1-like Proteins of *Bacillus subtilis* on Post-translocational Stages in Protein Secretion," *The Journal of Bioogical Chemistry*, 278(18):15622-15632 (2003).
Van Wely et al., "Translocation of proteins across the cell envelope of Gram-positive bacteria," *FEMS Microbiology Reviews*, 25:437-454 (2001).
The International Search Report for PCT/US02/39634 mailed Jul. 28, 2003.
Altamura et al., "*Saccharomyces cerevisiae OXA1* gene is requires for the correct assembly of cytochrome *c* oxidase and oligomycin-sensitive ATP synthase," *FEBS Letters*, 382:111-115 (1996).
Altschul et al., "Gapped BLAST and PSI-BLAST: a new generation of protein database search programs," *Nucleic Acids Research*, 25(17):3389-3402 (1997).
Antelmann et al., "A Proteomic View on Genome-Based Signal Peptide Predictions," *Genome Research*, 11:1484-1502 (2001).
Bauer et al., "*PET1402*, a nuclear gene required for proteolytic processing of cytochrome oxidase subunit 2 in yeast," *Mol. Gen. Genet.*, 245:272-278 (1994).

Bengtsson et al., "Subunit II of *Bacillus subtilis* Cytochrome *c* Oxidase Is a Lipoprotein," *Journal of Bacteriology*, 181(2):685-688 (1999).
Bolhuis et al., "SecDF of *Bacillus subtilis*, a Molecular Siamese Twin Required for the Efficient Secretion of Proteins," *The Journal of Biological Chemistry*, 273(33):21217-21224 (1998).
Bolhuis et al., "Functional Analysis of Paralogous Thiol-disulfide Oxidoreductases in *Bacillus subtilis*," *The Journal of Biological Chemistry*, 274(35):24531-24538 (1999).
Bonnefoy et al., "The respiratory gene *OXA1* has two fission yeast orthologues which together encode a function essential for cellular viability," *Molecular Microbiology*, 35(5):1135-1145 (2000).
Bonnefoy et al., "Cloning of a human gene involved in cytochrome oxidse assembly by functional complementation of an *oxa1* mutation in *Saccharomyces cerevisiae*," *Proc. Natl. Acad. Sci. USA*, 91:11978-11982 (1994).
Dalbey et al., "Evolutionary Related Insertion Pathways of Bacterial, Mitochondrial, and Thylakoid Membrane Proteins," *Annu. Rev. Cell Dev. Biol.*, 16:51-87 (2000).
Dalbey et al., "Protein translocation into and across the bacterial plasma membrane and the plant thylakoid membrane," *TIBS*, 24:17-21 (1999).
Dartois et al., "Genetic Analysis and Overexpression of Lipolytic Activity in *Bacillus subtilis*," *Applied and Environmental Microbiology*, 60(5):1670-1673 (1994).
de Gier et al., "Assembly of a cytoplasmic membrane protein in *Escherichia coli* is dependent on the signal recognition particle," *FEBS Letters*, 399:307-309 (1996).
Deuerling et al., "The *ftsH* gene of *Bacillus subtilis* is involved in major cellular processes such as sporulation, stress adaption and secretion", *Moecular Microbiology*, 23(5):921-933 (1997).
Errington et al., "Structure and function of the *spoIIIJ* gene of *Bacillus subtilis*: a vegetatively expressed gene that is essential for $\sigma^G$ activity at an Intermediate stage of sporulation," *Journal of General Microbiology*, 138:2609-2618 (1992).
Fekkes et al., "Protein Targeting to the Bacterial Cytoplasmic Membrane," *Microbiology and Molecular Biology Reviews*, 63(1):161-173 (1999).
Hale & Marham, *The Harper Collins Dictionary of Biology*, Harper Perennial, NY, 1991.
He et al., "Membrane Translocation of Mitochondrially coded Cox2p: Requirements for Export of N and C Termini and Dependence on the Conserved Protein Oxa1p," *Molecular Biology of the Cell*, 8:1449-1460 (1997).
Hell et al., "Oxa1p mediates the export of the N- and C-temini of pCoxII from the mitochondrial matrix to the intermembrane space," *FEBS Letters*, 418:367-370 (1997).

(Continued)

*Primary Examiner*—Nancy Vogel

(57) ABSTRACT

The present invention provides methods and compositions for the efficient and enhanced secretion of a protein of interest from a host cell. In specific, proteins are secreted through the Sec-dependent pathway, involving the spoIIIJ and/or yqjG gene product(s). In some embodiments, expression of the spoIIIJ and/or yqjG gene product(s) is modulated by a promoter operably linked to the gene.

9 Claims, 9 Drawing Sheets

OTHER PUBLICATIONS

Hell et al., "Oxa1p, an essential component of the N-tail protein export machinery in mitochondria," *Proc. Natl. Acad. Sci. USA*, 95:2250-2255 (1998).

Herrmann et al., "Insertion into the mitochondrial inner membrane of a polytopic protein, the nuclear-encoded Oxa1p," *The EMBO Journal*, 16(9):2217-2226 (1997).

Houben et al., "Nascent Lep inserts into the *Escherichia coli* inner membrane in the vicinity of YidC, SecY and SecA," *FEBS Letters*, 476:229-233 (2000).

Houben et al.,"YidC and SecY Mediate Membrane Insertion of a Type I Transmembrane Domain," *The Journal of Biological Chemistry*, 277(39):35880-35886 (2002).

Jacobs et al., "*Bacillus subtilis* PrsA is required in vivo as an extracytoplasmic chaperone for secretion of active enzymes synthesized either with or without pro-sequences," *Molecular Microbiology*, 8(5):957-966 (1993).

Jiang et al., "Differential processing of Propeptide Inhibitors of Rap Phosphatases in *Bacillus subtilis*," *Journal of Bacteriology*, 182(2):303-310 (2000).

Jongbloed et al., "TatC Is a Specificity Determinant for Protein Secretion via the Twin-arginine Translocation Pathway," *The Journal of Biological Chemistry*, 275(52):41350-41357 (2000).

Kontinen et al., "The PrsA lipoprotein is essential for protein secretion in *Bacillus subtilis* and sets a limit for high-level secretion," *Molecular Microbiology*, 8(4):727-737 (1993).

Kunst et al., "The complete genome sequence of the Gram-positive bacterium *Bacillus subtilis*," *Nature*, 390:249-264, (1997).

Kyhse-Andersen, "Electroblotting of multiple gels: a simple apparatus without buffer tank for rapid transfer of proteins from polyacrylamide to nitrocellulose," *Journal of Biochemical and Biophysical Methods*, 10:203-209 (1984).

Meijer et al., "The endogenous *Bacillus subtilis* (*natto*) plasmids pTA 1015 AND pTA 1040 contain signal peptidase-encoding genes : identification of a new structural module on cryptic plasmids," *Molecular Microbiology*, 17(4):621-631 (1995).

Miller, J. H., Experiments in Molecular Biology, Cold Spring Harbor Laboratory Press, Cold Spring Harbor NY (1982).

Moore et al., "Chloroplast Oxa1p Homolog Albino3 Is Required for Post-translational Integration of the Light Harvesting Chlorophyll-binding Protein into Thylakoid Membranes," *The Journal of Biological Chemistry*, 275(3):1529-1532 (2000).

Murakami et al., Analysis of the *Bacillus subtilis spoIIIJ* Gene and Its Paralogue Gene, yqG. *Journal of Bacteriology*, 184(7):1998-2004 (2002).

Palva, "Molecular cloning of α-amylase gene from *Bacillus amyloliquefaciens* and its expression in *B. subtilis*," *Gene*, 19:81-87 (1982).

Pogliano et al., "SecD and SecF facilitate protein export in *Escherichia coli*," *The EMBO Journal*, 13(3):554-561 (1994).

Pohlschröder et al., "Protein Translocation in the Three Domains of Life: Variations on a Theme," *Cell*, 91:563-566 (1997).

Prágai et al., "YsxC, a Putative GTP-Binding Protein Essential for Growth of *Bacillus subtilis* 168," *Journal of Bacteriology*, 182(23):6819-6823 (2000).

Prágai et al., "The signal peptidase II (*Isp*) gene of *Bacillus subtilis*," *Microbiology*, 143:1327-1333 (1997).

Robinson et al., "Protein Targeting by the Twin-Arginine Translocation Pathway," *Nature Reviews Molecular Cell Biology*, 2:350-356 (2001).

Sääf et al., "Membrane Topology of the 60-kDa Oxa1p Homologue from *Escherichia coli*," *The Journal of Biological Chemistry*, 273(46):30415-30418 (1998).

Sambrook, J. et al., Molecular Cloning, A Laboratory Manual, 2nd Ed., Cold Spring Harbor Laboratory Press, Cold Spring Harbor, New York, 1989.

Samuelson et al., "YidC mediates membrane protein insertion in bacteria," *Letters to Nature*, 406:637-641 (2000).

Schaeffer et al., "Catabolic Repression of Bacterial Sporulation," *Proc. Natl. Sci. USA*, 54:704-711 (1965).

Scotti et al., "YidC, the *Escherichia coli* homologue of mitochondrial Oxa1p, is a component of the Sec translocase," *The EMBO Journal*, 19(4) :542-549 (2000).

Singleton et al., Dictionary of Microbiology and Molecular Biology, $2^{nd}$ Ed., John Wiley and Sons, New York, 1994.

Sipos et al., "Predicting the topology of eukaryotic membrane proteins," *Eur. J. Biochem.*, 213:1333-1340 (1993).

Stuart et al., "Making membranes in bacteria ," *Nature*, 406:575, 577 (2000).

Tjalsma et al., "Functional analysis of the secretory precursor processing machinery of *Bacillus subtilis*: identification of a eubacterial homolog of archaeal and eukaryotic signal peptidases," *Genes & Develop.*, 12:2318-2331 (1998).

Tjalsma et al., "*Bacillus subtilis* Contains Four Closely Related Type I Signal Peptidases with Overlapping Substrate Specificities," *The J. Biol. Chem.*, 272(41):25983-25992 (1997).

Tjalsma et al., "The Role of Lipoprotein Processing by Signal Peptidase II in the Gram-positive Eubacterium *Bacillus subtilis*," *The J. Biol. Chem.*, 274(3):1698-1707 (1999).

Tjalsma et al., "Conserved Serine and Histidine Residues Are Critical for Activity of the ER-type Signal Peptidase SipW of *Bacillus subtilis*," *The Journal of Biological Chemistry*, 275(33):25102-25108 (2000).

Tjalsma et al., "Signal Peptide-Dependent Protein Transport in *Bacillus subtilis*: a Genome-Based Survey of the Secretome," *Microbiology and Molecular Biology Reviews*, 64(3):515-547 (2000).

Urbanus et al., Sec-dependent membrane protein insertion: sequential interaction of nascent FtsQ with SecY and YidC, *EMBO Reports*, 21(61):524-529 (2001).

Vagner et al., "A vector for systematic gene inactivation in *Bacillus subtilis*," *Microbiology*, 144:3097-3104 (1998).

Van Dijl et al., "Signal peptidase I overproduction results in increased eficiencies of export and maturation of hybrid secretory proteins in *Escherichia coli*," *Mol. Gen. Genet.*, 227:40-48 (1991).

Van Dijl et al., "Identification of the Potential Active Site of the Signal Peptidase SipS of *Bacillus subtilis*," *J. Biol. Chem.*, 270(8):3611-3618 (1995).

Van Dijl et al., "Non-functional expression of *Escherichia coli* signal peptidase I in *Bacillus subtilis*," *Journal of General Microbiology*, 137:2073-2083 (1991).

van Wely et al., "Functional Identification of the Product of the *Bacillus subtilis yvaL* Gene as a SecG Homologue," *Journal of Bacteriology*, 181(6):1786-1792 (1999).

van Wely et al., "The carboxyl terminus of the *Bacillus subtilis* SecA is dispensable for protein secretion and viability," *Microbiology*, 146:2573-2581 (2000).

Vieira et al., "New pUC-derived cloning vectors with different selectable markers and DNA replication origins," *Gene*, 100:189-194 (1991).

Wertman et al., "Host vector interactions which affect the viability of recombinant phage lambda clones," *Gene*, 49:253-262 (1986).

| | | |
|---|---|---|
| SpoIIIJ | MLLKRRIGLLLSMVGVFMLLAGCSSVKEPITADSPHFWDKYVVYPLSELITYVAKLTGDN---- | 63 |
| YqjG | ML-KTYQKLLAM---GIFLIVLCSGNAAFAATNQVGGLSNVGFFHDYLIEPFSALLKGVAGLFHGE | 65 |
| | I | |
| SpoIIIJ | YGLSIILVTILIRLLILPLMIKQLRSS----KAMQALQPEMQKLKEKYSS-KDQKTQQKLQQETMA | 121 |
| YqjG | YGLSIILVTIIIVRIVVLPLFVNQFKKQRIFQEKMAVIKPQVDSIQVKLKKTKDPEKQKELQMEMMK | 128 |
| YidC | WGFSIIIITFIVRGIMYPLTKAQYTSM----AKMRMLQPKIQAMRERL--GDD--KQRISQEMMA | 410 |
| Oxa1p | WWGTIAATTILIRCLMFFPLYVKSSDTV-----ARNSHIKPELDALNNKLMSTTDLQQGQLVAMQRKK | 189 |
| | II | |
| SpoIIIJ | LFQKHGVNP--LAG-CFPILIQMPILIGFYHAIMRTQAISEH-SFLWFDLGEKDPYYILP--IVA | 182 |
| YqjG | LYQEHNINP--LAMGCLPMLIQSPIMIGLYYAIRSTPEIASH-SFLWFSLGQSDIIMSLSAGIMY | 190 |
| YidC | LYKAEKVNP--LGG-CFPLLIQMPIFLALYYMLGSVELRQAPFALWIHDLSAQDPYYILP--ILM | 473 |
| Oxa1p | LLSSHGIKNRWLAAPMLQIPIALGFFNALRHMANYPVDGFANQGVAWFTDLTQADPYLGLQVITAA | 255 |
| | IV V | |
| SpoIIIJ | GVATFVQQKLMMAGNAQQNP----QMAMMLWIMPIMIIVFAINFPAALSLYWVVGNLFMIAQTFL | 241 |
| YqjG | FVQAYIAQKLSAKYSAVPQNPAAQQSAKLMVFIFPVMMTIFSLNVPAALPLYWFTSGLFLTVQNIV | 256 |
| YidC | GVTMFFIQKMSPT--TVTDP----MQQKIMTFMPVIFTVFFLWEPSGLVLYYIVSNLVTIIQQQL | 532 |
| Oxa1p | VFISFTRLGGETGAQQFSSP----MKRLFTILPIISIPATMNLSSAVVLYFAFNGAFSVLQTMI | 315 |
| SpoIIIJ | IKGPDIKKNPEPQKAGGKKK | 261 |
| YqjG | LQMTHHKSKKTAALTESV-K | 275 |

FIG._1A

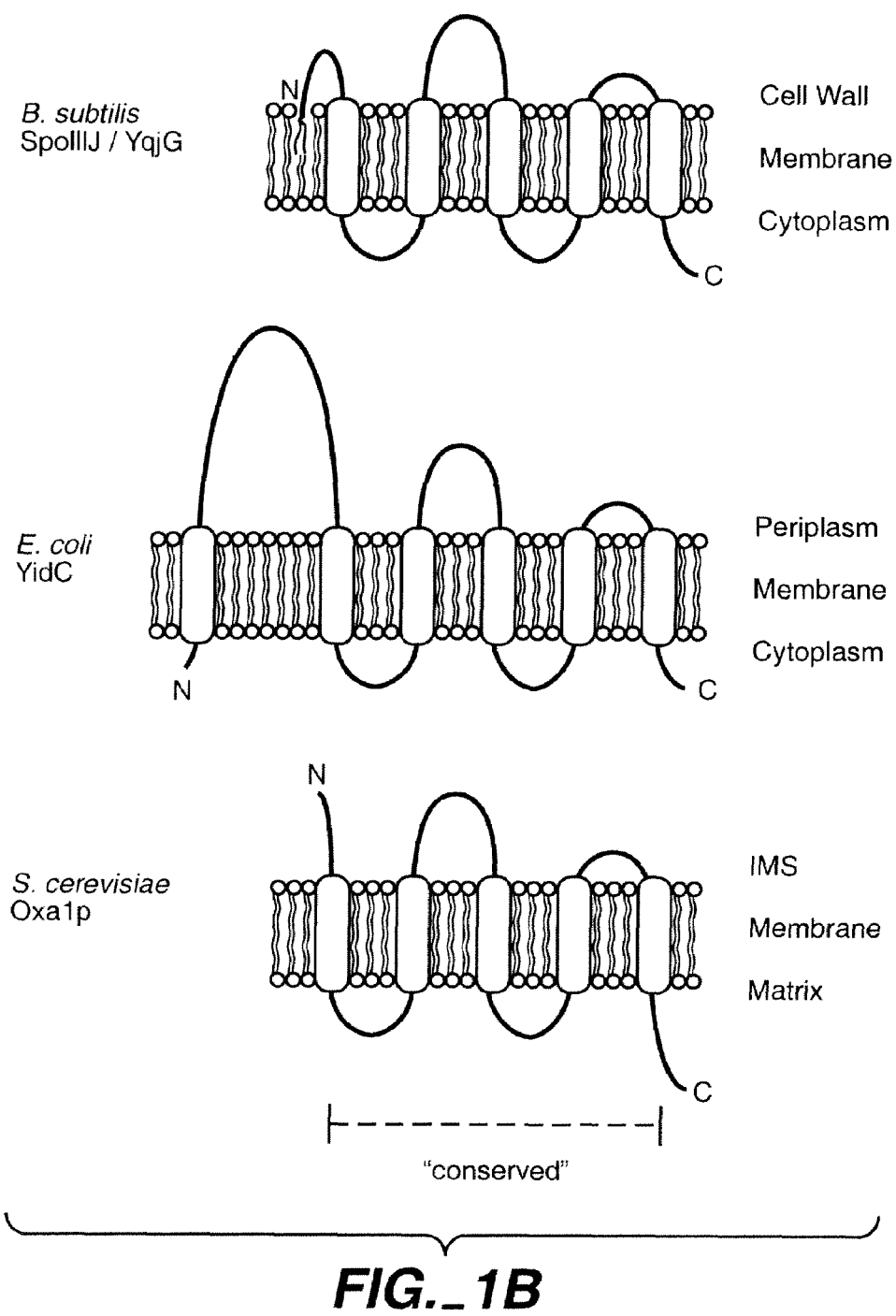
FIG._1B

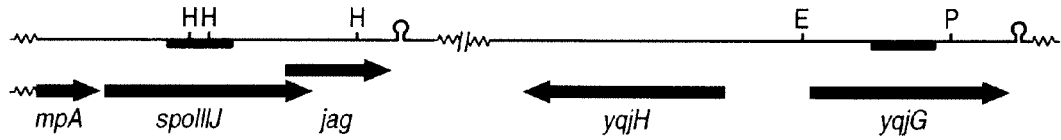
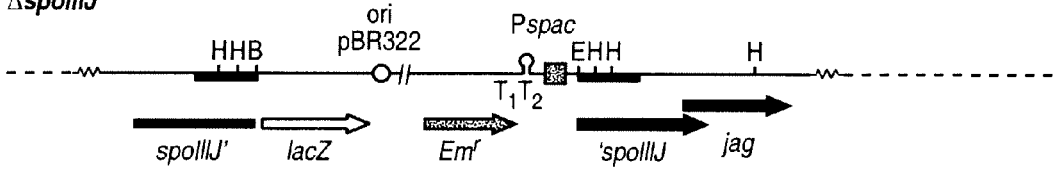
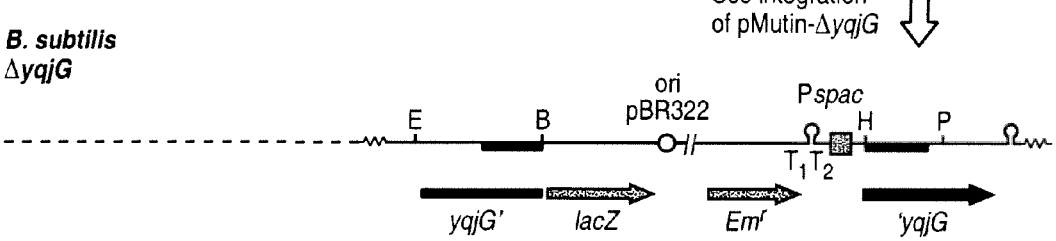
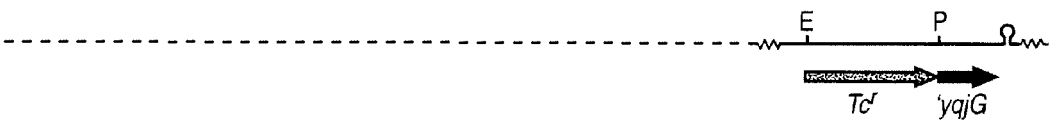
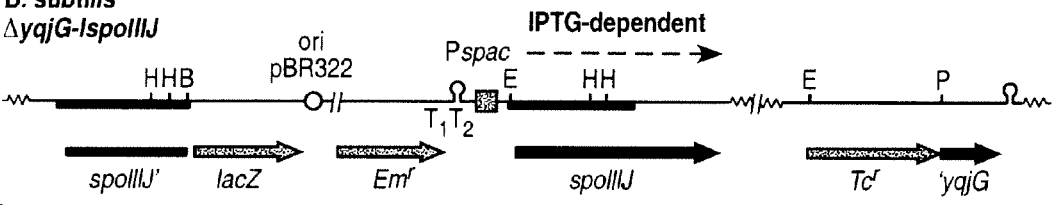
FIG._2

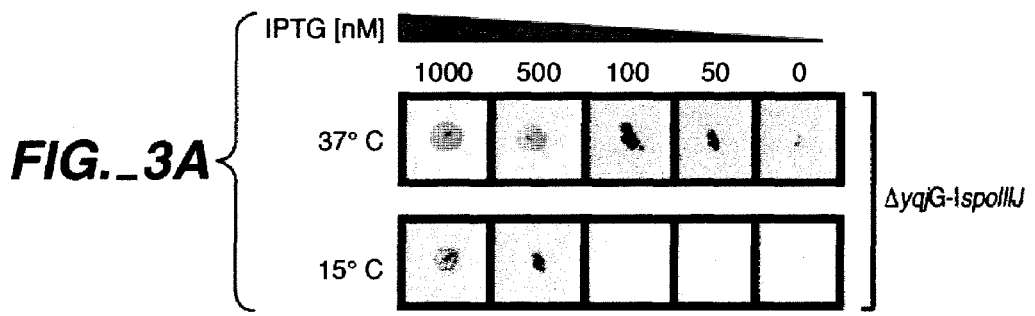
FIG._3A
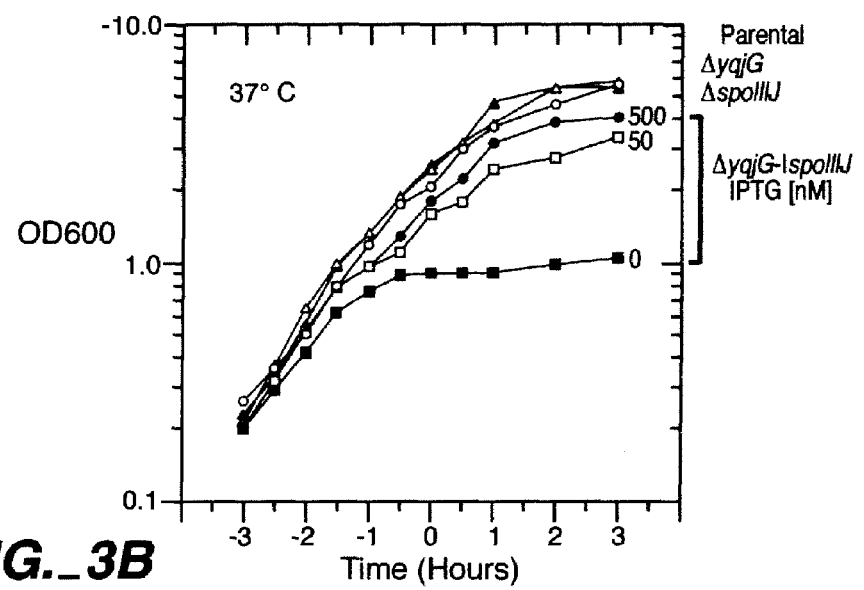
FIG._3B
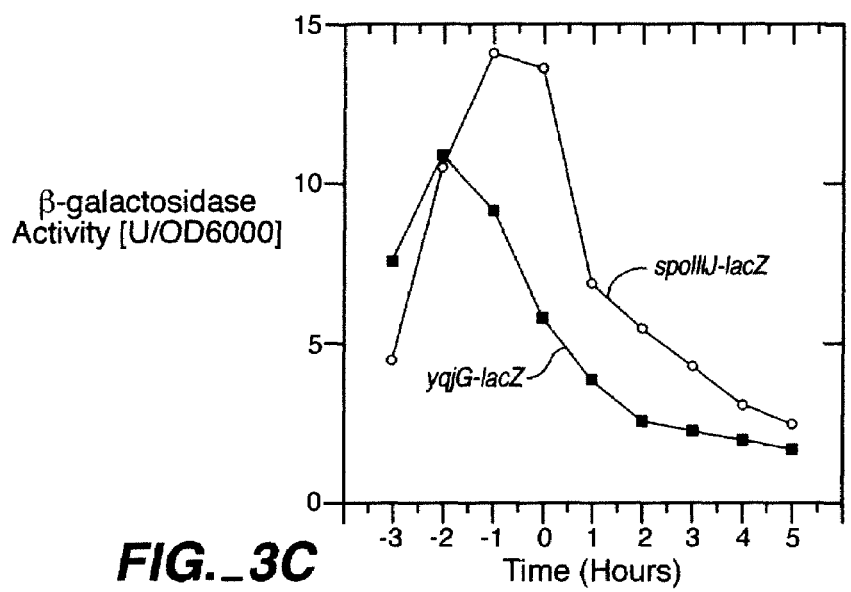
FIG._3C

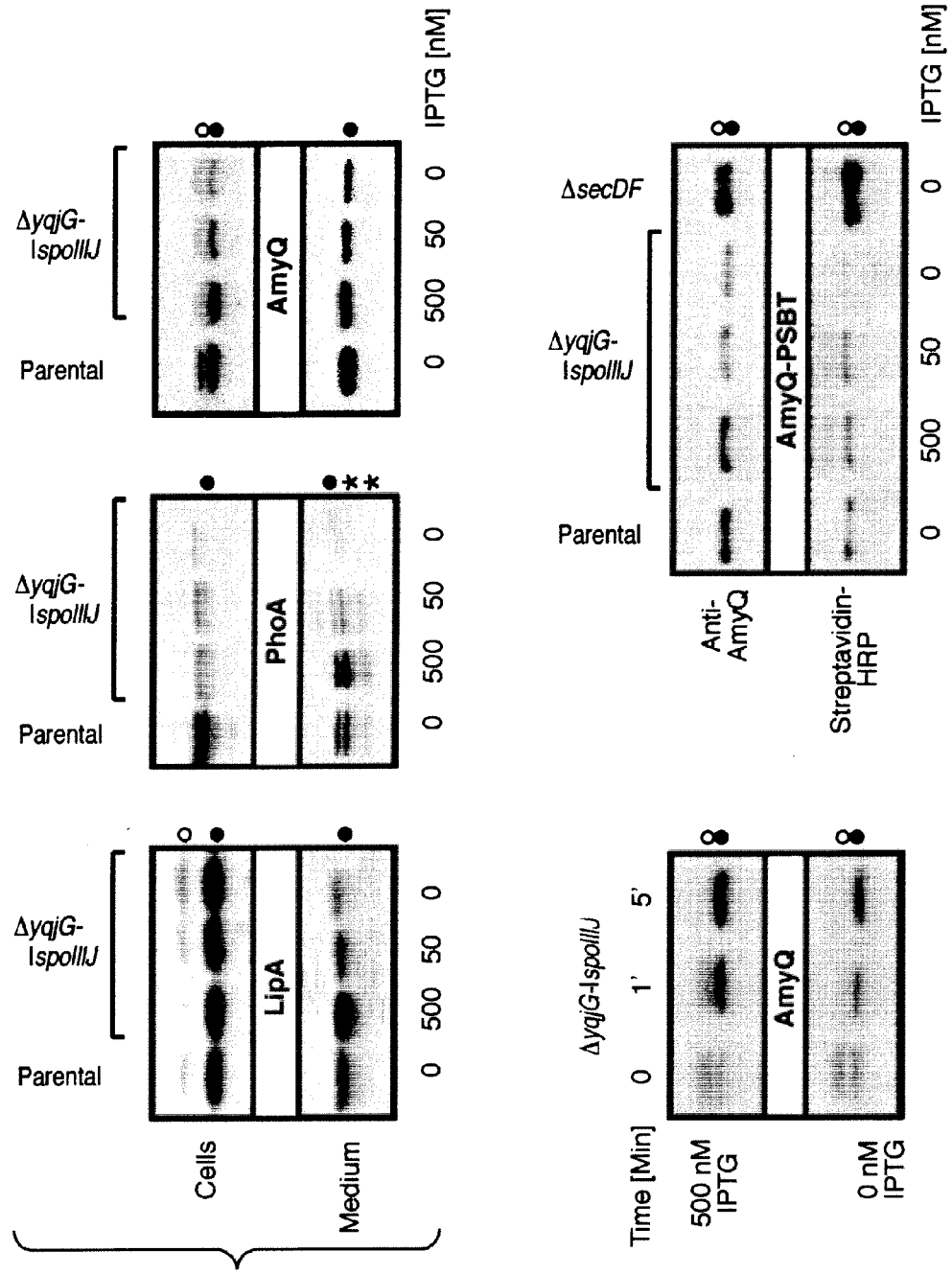

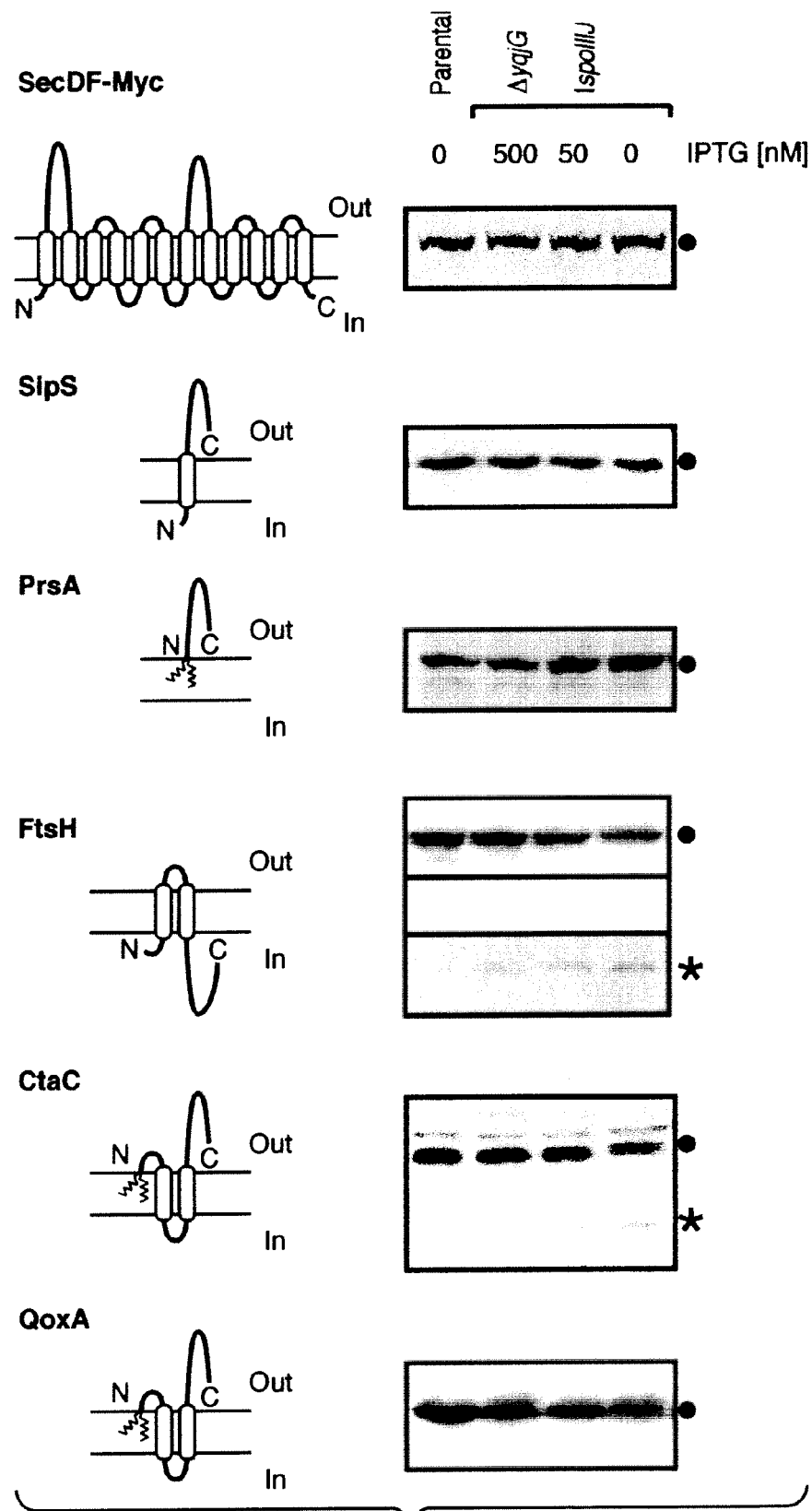
FIG._6

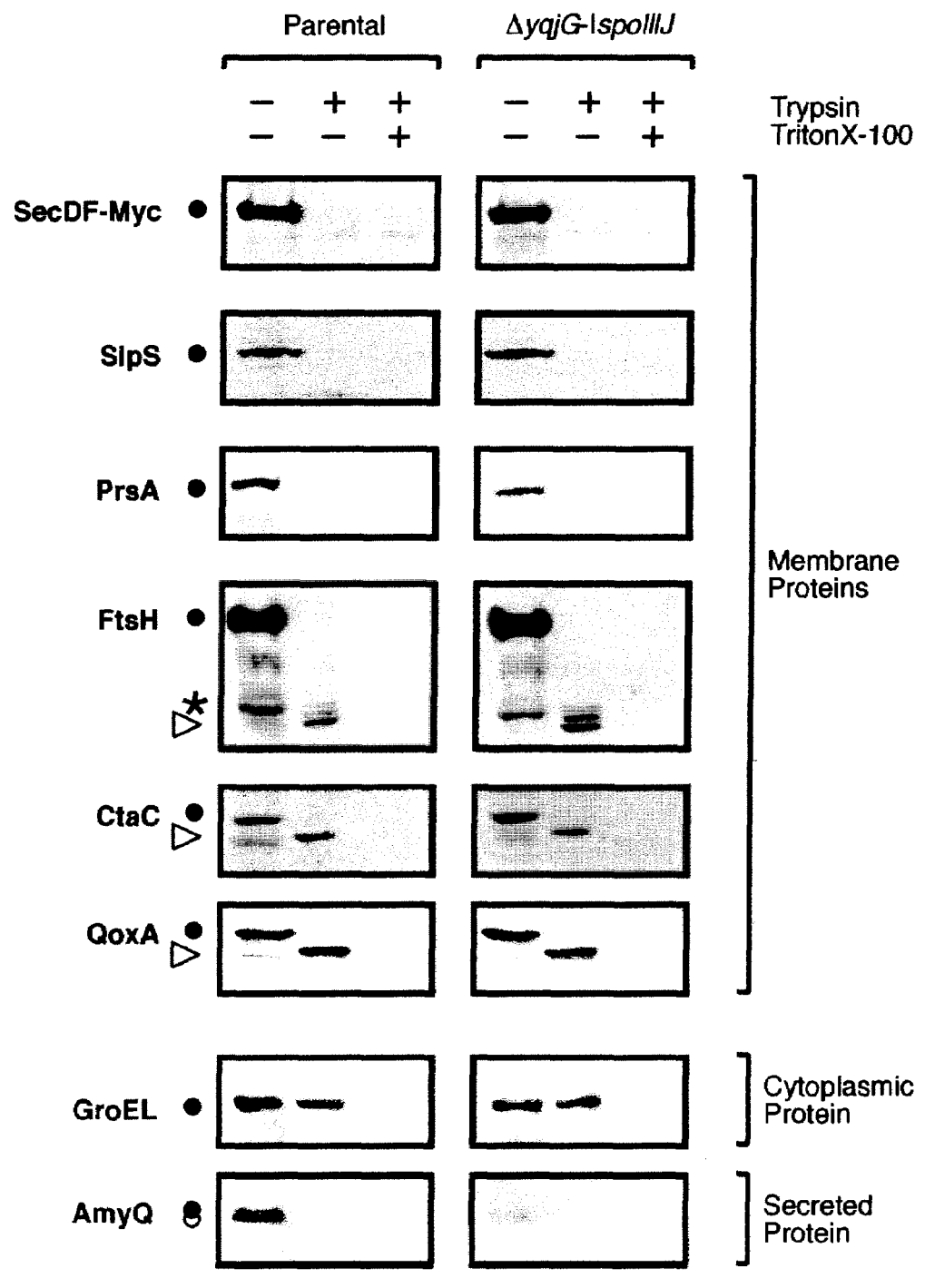
FIG._7

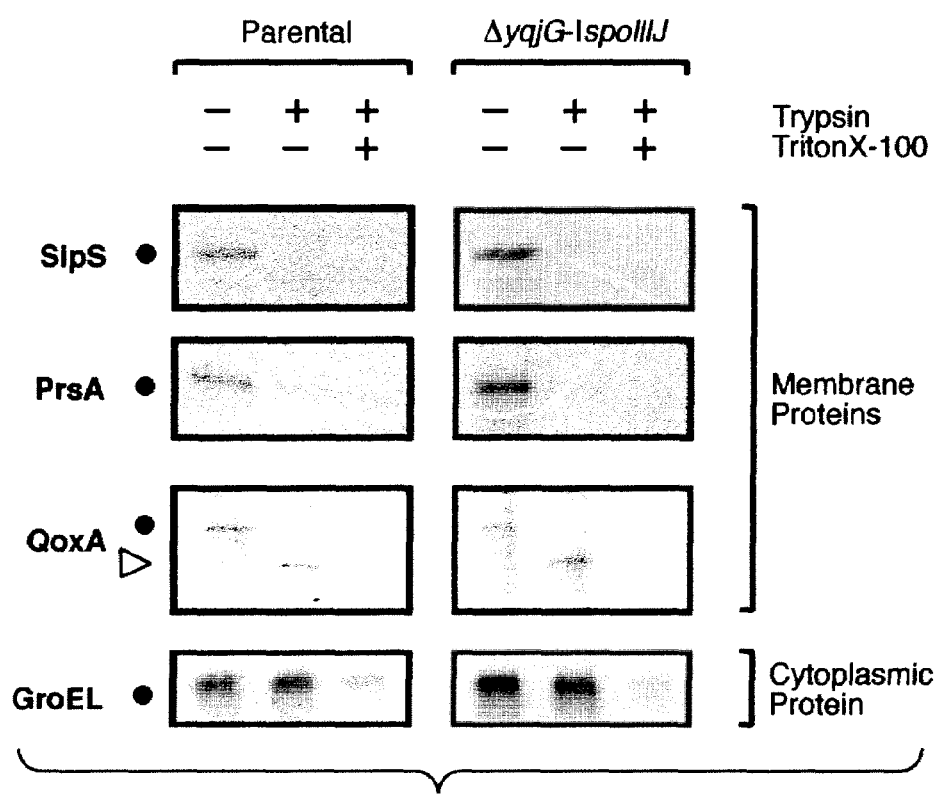
FIG._8

SEQUENCE LISTING

<160> NUMBER OF SEQ ID NOS: 11

<210> SEQ ID NO 1
<211> LENGTH: 28
<212> TYPE: DNA
<213> ORGANISM: Artificial Sequence
<220> FEATURE:
<223> OTHER INFORMATION: primer

<400> SEQUENCE: 1
gagaattcga cgggagataa ctacgggc                                      28

<210> SEQ ID NO 2
<211> LENGTH: 29
<212> TYPE: DNA
<213> ORGANISM: Artificial Sequence
<220> FEATURE:
<223> OTHER INFORMATION: primer

<400> SEQUENCE: 2
atggatccta tgctctgaaa tcgcctggg                                     29

<210> SEQ ID NO 3
<211> LENGTH: 25
<212> TYPE: DNA
<213> ORGANISM: Artificial Sequence
<220> FEATURE:
<223> OTHER INFORMATION: primer

<400> SEQUENCE: 3
tgaagcttgc cgggctgttt cacgg                                         25

<210> SEQ ID NO 4
<211> LENGTH: 32
<212> TYPE: DNA
<213> ORGANISM: Artificial Sequence
<220> FEATURE:
<223> OTHER INFORMATION: primer

<400> SEQUENCE: 4
atggatccat cgtcatcatc acagggaaga tg                                 32

<210> SEQ ID NO 5
<211> LENGTH: 24
<212> TYPE: DNA
<213> ORGANISM: Artificial Sequence
<220> FEATURE:
<223> OTHER INFORMATION: primer

<400> SEQUENCE: 5
gctttggatt tcttttgccg tctc                                          24

```
<210> SEQ ID NO 6
<211> LENGTH: 23
<212> TYPE: DNA
<213> ORGANISM: Artificial Sequence
<220> FEATURE:
<223> OTHER INFORMATION: primer

<400> SEQUENCE: 6
ggttcgtgag cataaaggga agc                                           23

<210> SEQ ID NO 7
<211> LENGTH: 42
<212> TYPE: DNA
<213> ORGANISM: Artificial Sequence
<220> FEATURE:
<223> OTHER INFORMATION: primer

<400> SEQUENCE: 7
ggaattctag agtgtaaaga ttaattatag gaggaaatgt tg                      42

<210> SEQ ID NO 8
<211> LENGTH: 261
<212> TYPE: PRT
<213> ORGANISM: Bacillus subtilis

<400> SEQUENCE: 8
```

Met Leu Leu Lys Arg Arg Ile Gly Leu Leu Ser Met Val Gly Val
 1               5                  10                  15

Phe Met Leu Leu Ala Gly Cys Ser Ser Val Lys Glu Pro Ile Thr Ala
             20                  25                  30

Asp Ser Pro His Phe Trp Asp Lys Tyr Val Val Tyr Pro Leu Ser Glu
         35                  40                  45

Leu Ile Thr Tyr Val Ala Lys Leu Thr Gly Asp Asn Tyr Gly Leu Ser
     50                  55                  60

Ile Ile Leu Val Thr Ile Leu Ile Arg Leu Leu Ile Leu Pro Leu Met
 65                  70                  75                  80

Ile Lys Gln Leu Arg Ser Ser Lys Ala Met Gln Ala Leu Gln Pro Glu
                 85                  90                  95

Met Gln Lys Leu Lys Glu Lys Tyr Ser Ser Lys Asp Gln Lys Thr Gln
            100                 105                 110

Gln Lys Leu Gln Gln Glu Thr Met Ala Leu Phe Gln Lys His Gly Val
        115                 120                 125

Asn Pro Leu Ala Gly Cys Phe Pro Ile Leu Ile Gln Met Pro Ile Leu
    130                 135                 140

Ile Gly Phe Tyr His Ala Ile Met Arg Thr Gln Ala Ile Ser Glu His
145                 150                 155                 160

Ser Phe Leu Trp Phe Asp Leu Gly Glu Lys Asp Pro Tyr Tyr Ile Leu
                165                 170                 175

Pro Ile Val Ala Gly Val Ala Thr Phe Val Gln Gln Lys Leu Met Met
            180                 185                 190

Ala Gly Asn Ala Gln Gln Asn Pro Gln Met Ala Met Met Leu Trp Ile
        195                 200                 205

Met Pro Ile Met Ile Ile Val Phe Ala Ile Asn Phe Pro Ala Ala Leu
    210                 215                 220

Ser Leu Tyr Trp Val Val Gly Asn Leu Phe Met Ile Ala Gln Thr Phe
225                 230                 235                 240

Leu Ile Lys Gly Pro Asp Ile Lys Lys Asn Pro Glu Pro Gln Lys Ala
                245                 250                 255

```
Gly Gly Lys Lys Lys
         260

<210> SEQ ID NO 9
<211> LENGTH: 275
<212> TYPE: PRT
<213> ORGANISM: Bacillus subtilis

<400> SEQUENCE: 9

Met Leu Lys Thr Tyr Gln Lys Leu Leu Ala Met Gly Ile Phe Leu Ile
 1               5                  10                  15

Val Leu Cys Ser Gly Asn Ala Ala Phe Ala Ala Thr Asn Gln Val Gly
            20                  25                  30

Gly Leu Ser Asn Val Gly Phe Phe His Asp Tyr Leu Ile Glu Pro Phe
        35                  40                  45

Ser Ala Leu Leu Lys Gly Val Ala Gly Leu Phe His Gly Glu Tyr Gly
    50                  55                  60

Leu Ser Ile Ile Leu Val Thr Ile Ile Val Arg Ile Val Leu Pro
65                  70                  75                  80

Leu Phe Val Asn Gln Phe Lys Lys Gln Arg Ile Phe Gln Glu Lys Met
                85                  90                  95

Ala Val Ile Lys Pro Gln Val Asp Ser Ile Gln Val Lys Leu Lys Lys
            100                 105                 110

Thr Lys Asp Pro Glu Lys Gln Lys Glu Leu Gln Met Glu Met Met Lys
        115                 120                 125

Leu Tyr Gln Glu His Asn Ile Asn Pro Leu Ala Met Gly Cys Leu Pro
    130                 135                 140

Met Leu Ile Gln Ser Pro Ile Met Ile Gly Leu Tyr Tyr Ala Ile Arg
145                 150                 155                 160

Ser Thr Pro Glu Ile Ala Ser His Ser Phe Leu Trp Phe Ser Leu Gly
                165                 170                 175

Gln Ser Asp Ile Leu Met Ser Leu Ser Ala Gly Ile Met Tyr Phe Val
            180                 185                 190

Gln Ala Tyr Ile Ala Gln Lys Leu Ser Ala Lys Tyr Ser Ala Val Pro
        195                 200                 205

Gln Asn Pro Ala Ala Gln Gln Ser Ala Lys Leu Met Val Phe Ile Phe
    210                 215                 220

Pro Val Met Met Thr Ile Phe Ser Leu Asn Val Pro Ala Ala Leu Pro
225                 230                 235                 240

Leu Tyr Trp Phe Thr Ser Gly Leu Phe Leu Thr Val Gln Asn Ile Val
                245                 250                 255

Leu Gln Met Thr His His Lys Ser Lys Lys Thr Ala Ala Leu Thr Glu
            260                 265                 270

Ser Val Lys
        275

<210> SEQ ID NO 10
<211> LENGTH: 177
<212> TYPE: PRT
<213> ORGANISM: Escherichia coli

<400> SEQUENCE: 10

Trp Gly Phe Ser Ile Ile Ile Thr Phe Ile Val Arg Gly Ile Met
 1               5                  10                  15

Tyr Pro Leu Thr Lys Ala Gln Tyr Thr Ser Met Ala Lys Met Arg Met
            20                  25                  30
```

Leu Gln Pro Lys Ile Gln Ala Met Arg Glu Arg Leu Gly Asp Asp Lys
             35                  40                  45

Gln Arg Ile Ser Gln Glu Met Met Ala Leu Tyr Lys Ala Glu Lys Val
 50                  55                  60

Asn Pro Leu Gly Gly Cys Phe Pro Leu Leu Ile Gln Met Pro Ile Phe
 65                  70                  75                  80

Leu Ala Leu Tyr Tyr Met Leu Met Gly Ser Val Glu Leu Arg Gln Ala
                 85                  90                  95

Pro Phe Ala Leu Trp Ile His Asp Leu Ser Ala Gln Asp Pro Tyr Tyr
            100                 105                 110

Ile Leu Pro Ile Leu Met Gly Val Thr Met Phe Phe Ile Gln Lys Met
            115                 120                 125

Ser Pro Thr Thr Val Thr Asp Pro Met Gln Gln Lys Ile Met Thr Phe
            130                 135                 140

Met Pro Val Ile Phe Thr Val Phe Phe Leu Trp Glu Pro Ser Gly Leu
145                 150                 155                 160

Val Leu Tyr Tyr Ile Val Ser Asn Leu Val Thr Ile Ile Gln Gln Gln
                165                 170                 175

Leu

<210> SEQ ID NO 11
<211> LENGTH: 188
<212> TYPE: PRT
<213> ORGANISM: Saccharomyces cerevisiae

<400> SEQUENCE: 11

Trp Trp Gly Thr Ile Ala Ala Thr Thr Ile Leu Ile Arg Cys Leu Met
 1               5                  10                  15

Phe Pro Leu Tyr Val Lys Ser Ser Asp Thr Val Ala Arg Asn Ser His
                 20                  25                  30

Ile Lys Pro Glu Leu Asp Ala Leu Asn Asn Lys Leu Met Ser Thr Thr
             35                  40                  45

Asp Leu Gln Gln Gly Gln Leu Val Ala Met Gln Arg Lys Lys Leu Leu
 50                  55                  60

Ser Ser His Gly Ile Lys Asn Arg Trp Leu Ala Ala Pro Met Leu Gln
 65                  70                  75                  80

Ile Pro Ile Ala Leu Gly Phe Phe Asn Ala Leu Arg His Met Ala Asn
                 85                  90                  95

Tyr Pro Val Asp Gly Phe Ala Asn Gln Gly Val Ala Trp Phe Thr Asp
            100                 105                 110

Leu Thr Gln Ala Asp Pro Tyr Leu Gly Leu Gln Val Ile Thr Ala Ala
            115                 120                 125

Val Phe Ile Ser Phe Thr Arg Leu Gly Gly Glu Thr Gly Ala Gln Gln
            130                 135                 140

Phe Ser Ser Pro Met Lys Arg Leu Phe Thr Ile Leu Pro Ile Ile Ser
145                 150                 155                 160

Ile Pro Ala Thr Met Asn Leu Ser Ser Ala Val Val Leu Tyr Phe Ala
                165                 170                 175

Phe Asn Gly Ala Phe Ser Val Leu Gln Thr Met Ile
            180                 185

OXA1P ENHANCED PROTEIN SECRETION

FIELD OF THE INVENTION

The present invention provides methods and compositions for the efficient and enhanced secretion of a protein of interest from a host cell. In specific, proteins are secreted through the Sec-dependent pathway, involving the spoIIIJ and/or yqjG gene product(s). In some embodiments, expression of the spoIIIJ and/or yqjG gene product(s) is modulated by a promoter operably linked to the gene.

BACKGROUND OF THE INVENTION

In recent years, not only interesting similarities, but also striking differences between protein transport pathways in eubacteria, archaea, eukaryotes, and eukaryotic organelles have been documented (Pohlschröder et al., Cell 91:563-566 [1997]; Dalbey and Robinson, Trends Biochem. Sci., 24:17-22 [1999]; and Dalbey and Kuhn, Ann. Rev. Cell. Dev. Biol., 16:51-87 [2000]). Insights into the extent of conservation and divergence in these pathways were provided due to the availability of many complete genome sequences. Unfortunately, the biological significance of such insights has often proven difficult, to test as the majority of organisms with sequenced genomes are poorly amenable to biochemical or genetic approaches. In this respect, the Gram-positive eubacterium *Bacillus subtilis,* the complete genome sequence of which was published by Kunst et al. (Kunst et al., Nature 390:249-356 [1997]), has been a very useful exception, due to this organism's natural system for genetic transformation and its large capacity for the secretion of proteins directly into the growth medium (See, Tjalsma et al., Microbiol. Mol. Biol. Rev., 64:515-547 [2000a]). Nonetheless, much remains unknown regarding the biosynthetic pathways of *Bacillus.*

The functional genomic approach to dissect the protein secretion process in *B. subtilis* has yielded a number of remarkable surprises. These surprises include striking differences in the composition of the general secretion (Sec) and twin-arginine translocation (Tat) pathways for the transport of secretory pre-proteins across the membranes of *B. subtilis* and *E. coli* (Bolhuis et al., J. Biol. Chem., 273:21217-21224 [1998]; Bolhuis et al., J. Biol. Chem., 274:24531-24538 [1999a]; Jongbloed et al., J. Biol. Chem., 275:41350-41357 [2000]; Robinson and Bolhuis, Nat. Rev. Mol. Cell. Biol., 2:350-356 [2001]; and van Wely et al., Microbiol., 146:2573-2581 [2000]).

In contrast to *Escherichia coil* (See, Fekkes and Driessen, Microbiol. Mol. Biol. Rev., 63:161-173 [1999]), the Sec-dependent translocation machinery of *B. subtilis* lacks a SecB component (van Wely et al., J. Bacteriol., 181:1786-1792 [2000]). Moreover, the *B. subtilis* SecDF component, which is present as a natural fusion protein, is merely required to optimize the efficiency of protein translocation under conditions of protein hyper-secretion at gram per litre levels (Bolhuis et al., [1998], supra), while the separate SecD and SecF proteins of *E. coli* are very important both for protein export and cell viability (Pogliano and Beckwith, EMBO J., 13:554-561 [1994]). In addition, in contrast to the twin-arginine translocation (Tat) machinery of *E. coli* that consists of the unique TatB and TatC components and the paralogous TatA and TatE components (See e.g., Robinson and Bolhuis, Nat. Rev. Mol. Cell. Biol., 2:350-356 [2001]), the Tat machinery of *B. subtilis* lacks distinguishable TatA/E and TatB components, while two paralogous TatC proteins with distinct functions are present (Jongbloed et al., [2000], supra).

Translocated pre-proteins of *B. subtilis* with Sec-type or twin-arginine signal peptides have been shown to be subject to processing by the largest number of type I signal peptidases (SPases) known in various organisms. In addition to five chromosomally-encoded SPases (SipS, SipT, SipU, SipV, and SipW [Tjalsma et al., Genes Dev., 12:2318-2331 (1998)]), some *B. subtilis* strains contain plasmid-encoded SPases (Meijer et al., Mol. Microbiol., 17:621-631 [1995]). Furthermore, SipW was the first known eubacterial SPase of a type that is mainly encountered in archaea and the eukaryotic endoplasmic reticular membrane (Tjalsma et al., [1998], supra; and Tjalsma et al., J. Biol. Chem., 275:25102-25108 [2000b]).

Another finding was that the unique type II SPase (Lsp) of *B. subtilis* (Prágai et al., Microbiol., 143:1327-1333 [1997]), which specifically catalyzes the maturation of lipid-modified pre-proteins is required for the secretion of non-lipoproteins, such as α-amylase, chitosanase, and lipase (Tjalsma et al., J. Biol. Chem., 274:1698-1707 [1999]; and Antelmann et al., Genome Res., 11:1484-1502 [2001]). When the negative effect of an lsp mutation on non-lipoprotein secretion was first observed for the α-amylase AmyQ, it was largely attributed to a possible malfunctioning of the lipoprotein PrsA, which is essential for the proper folding of various translocated proteins, such as AmyQ.

In addition, the original view that Gram-positive eubacteria would lack thiol-disulfide oxidoreductases for the formation of disulfide bonds in secretory proteins was disproved with the identification of three Bdb proteins (Bolhuis et al., J. Biol. Chem., 274:24531-24538 [1999b]). Indeed, any lesson learned regarding protein secretion and the relative contribution of homologs from Gram-negative bacteria is not necessarily be relevant to Gram-positive microorganisms. Thus, there remains a need in the art to provide means to assess and identify secretory proteins in Gram-positive organisms such as *Bacillus*.

SUMMARY OF THE INVENTION

The present invention provides methods and compositions for the efficient secretion of proteins from Gram-positive microorganisms.

In some preferred embodiments, the present invention provides DNA constructs for the inducible expression of the spoIIIJ and/or yqjG gene(s). In particularly preferred embodiments, the spoIIIJ and/or yqjG gene(s) is/are operably linked to a promoter sequence. In some embodiments, the promoter is inducible, while in other embodiments the promoter is constitutive.

In some embodiments, a second DNA sequence is inserted into the host cell. In preferred embodiments, the second sequence encodes a Sec-dependent signal sequence that is inked or fused to a protein of interest. In some embodiments, the protein of interest is homologous, while in other embodiments, it is heterologous to the host cell.

The present invention further provides methods for modulating Sec-dependent protein secretion comprising the steps of: introducing a spoIIIJ gene linked to an inducible promoter into a *Bacillus* cell; and modulating the expression of the spoIIIJ gene by varying the level of induction of the inducible promoter. In some embodiments, the inducible promoter is the Pspac promoter. In alternative embodiments, the methods of inhibiting sporulation in a *Bacillus* cell, comprise a mutation of the spoIIIJ gene wherein the mutation results in the formation of an inactive gene product. In additional embodiments, the present invention provides purified DNA molecules comprising an inducible promoter operatively linked to the spoIIIJ gene.

The present invention also provides methods for modulating the secretion of a protein of interest, comprising the steps of: forming a first DNA molecule encoding a chimeric protein comprising a Sec-dependent secretion signal peptide; forming a second DNA molecule encoding an inducible promoter operably linked to the spoIIIJ gene; transforming a host cell with the DNA molecule of steps the previous steps; and growing the host cell under conditions wherein the protein of interest is expressed at the desired level. In some embodiments, the host cell is grown under conditions wherein the inducible promoter is induced. In still further embodiments, the protein of interest is expressed at low level.

The present invention further provides methods of modulating Sec-dependent protein secretion comprising the steps of: introducing a yqjG gene linked to an inducible promoter into a Bacillus cell; and modulating the expression of the yqjG gene by varying the level of induction of the inducible promoter. In some embodiments, the inducible promoter is the Pspac promoter.

The present invention also provides methods of inhibiting sporulation in a *Bacillus* cell, wherein the methods comprise a mutation of the spoIIIJ gene wherein the mutation results in the formation of an inactive gene product. In still further embodiments, the present invention provides purified DNA molecules comprising an inducible promoter operatively linked to the yqjG gene.

The present invention further provides methods for modulating the secretion of a protein of interest, comprising the steps of: forming a first DNA molecule encoding a chimeric protein comprising a Sec-dependent secretion signal peptide; forming a second DNA molecule encoding an inducible promoter operably linked to the yqjG gene; transforming a host cell with the DNA molecule of steps the previous steps; and growing the host cell under conditions wherein the protein of interest is expressed at the desired level. In some embodiments, the host cell is grown under conditions wherein the inducible promoter is induced. In still further embodiments, the protein of interest is expressed at low level.

The present invention also provides methods of modulating Sec-dependent protein secretion comprising the steps of: providing a *Bacillus* cell comprising spoIIIJ and yqjG genes linked to an endogenous high expression promoter; and modulating the expression of the spoIIIJ and yqjG genes by varying the level of induction of the promoter. In some embodiments, the promoter is the Pspac promoter.

Other objects, features and advantages of the present invention will become apparent from the present Specification. It should be understood, however, that the detailed description and specific examples, while indicating preferred embodiments of the invention, are given by way of illustration only, since various changes and modifications within the scope and spirit of the invention will become apparent to one skilled in the art from this detailed description.

DESCRIPTION OF THE FIGURES

FIG. 1, Panel A provides a sequence comparison showing the conservation of Oxa1p(-like) proteins in *B. subtilis, E. coli* and mitochondria of the yeast *S. cerevisiae*. In this Panel, the amino acid sequences of SpoIIIJ (SEQ ID NO:8) and YqjG (SEQ ID NO:9), and the partial sequences of YidC (SEQ ID NO:10) and Oxa1p (SEQ ID NO:11), comprising the conserved part as depicted in Panel B are shown. Identical residues are indicated in bold. The conserved transmembrane segments I-V (marked in gray shading) was predicted as described by Sipos and von Heijne (Sipos and von Heijne, Eur. J. Biochem., 213:1333-1340 [1993]). The putative SPase II cleavage sites (lipoboxes) in SpoIIIJ and YqjG are underlined. Notably, SpoIIIJ/YqjG orthologues with putative lipoprotein signal peptides have been found in several Gram-positive eubacteria (during the development of the present invention, SpoIIIJ/YQJG orthologues with putative lipoprotein signal peptides were identified in *B. anthracis, B. halodurans, B. stearothermophilus, Lactococcus lactis,* and *Staphylococcus aureus*). In this Panel, the numbers refer to the position of amino acids in the corresponding protein sequence.

FIG. 1, Panel B, provides the predicted membrane topologies of SpoIIIJ and YqjG of *B. subtilis*, YidC of *E. coli*, and Oxa1p of *S. cerevisiae*. Only the membrane topology of YidC has been verified experimentally (Saaf et al., J. Biol. Chem., 273:30415-30418 [1998]). Notably, the YidC protein has a large amino-terminal loop located in the periplasm that is absent from SpoIIIJ, YqjG and Oxa1p. The abbreviations used in this Figure are: C, carboxyl-terminus; the cytoplasmic, cell wall, periplasmic, matrix, or inter membrane space (IMS) sides of the membranes, and the "conserved" parts of the Oxa1p(-like) proteins are indicated. In addition, as shown in this Figure, the amino-termini of SpoIIIJ and YqjG are most likely lipid-modified.

FIG. 2 shows the construction of spoIIIJ and/or yqjG mutant strains of *B. subtilis*. As indicated, *B. subtilis* ΔspoIIIJ and *B. subtilis* ΔyqjG were respectively, constructed by the single cross-over integration of pMutin-ΔspoIIIJ and pMutin-ΔyqjG into the chromosome *B. subtilis* 168. In these strains, the respective spoIIIJ or yqjG genes are disrupted while the lacZ gene of pMutin2 is placed under the transcriptional control of the promoter regions of these genes. *B. subtilis* ΔyqjG-Tc was constructed by replacement of the 5' part of the yqjG gene with a tetracycline resistance marker by double cross-over recombination. *B. subtilis* ΔyqjG-IspoIIIJ was constructed by integration of pMutin-IspoIIIJ into the spoIIIJ region of *B. subtilis* ΔyqjG-Tc. Using this approach, the spoIIIJ gene was placed under the control of the (IPTG)-dependent Pspac promoter. Notably, growth and viability of the latter strain is dependent on the presence of IPTG. The relative positions of open reading frames in the spoIIIJ and yqjG regions are shown. PCR-amplified DNA fragments that were used to direct the integration of pMutin2 into the *B. subtilis* chromosome are indicated with black bars. The abbreviations (including restriction sites relevant for the construction) used in this Figure are: B, BamHI; dco, double cross-over, E, EcoRI; H, HindIII; jag, gene of unknown function specifying a predicted cytoplasmic protein; P, PstI. Ori pBR322, replication functions of pBR322; Emr, erythromycin resistance marker; sco, single cross-over; T1T2, transcriptional terminators on pMutin2; spoIIIJ', 3' truncated spoIIIJ gene; 'spoIIIJ, 5' truncated spoIIIJ gene; yqjG', 3' truncated yqjG gene; and 'yqjG, 5' truncated yqjG gene.

FIG. 3 depicts properties of spoIIIJ and/or yqjG mutant strains of *B. subtilis*. In Panel A, IPTG-dependent growth of *B. subtilis* ΔyqjG-IspoIIIJ on plates incubated at 15° C. and 37° C. is shown. Individual colonies of *B. subtilis* ΔyqjG-IspoIIIJ were transferred to fresh TY-agar plates containing 1000, 500, 100, 50, or 0 nM IPTG. Next, the plates were incubated overnight at 37° C. (upper panel), or for 5 days at 15° C. (lower panel).

FIG. 3, Panel B shows the IPTG-dependent growth of *B. subtilis* ΔyqjG-IspoIIIJ. Overnight cultures of *B. subtilis* 168 (parental; Δ), *B. subtilis* ΔspoIIIJ (▲), *B. subtilis* ΔyqjG (○) and *B. subtilis* ΔyqjGIspoIIIJ (■), grown in TY medium at 37° C., were washed and diluted 20-fold in fresh TY medium without IPTG and incubated at 37° C. In addition, *B. subtilis* ΔyqjG-IspoIIIJ was diluted in fresh TY medium containing 50 (□) or 500 (●) nM IPTG. Zero time (t=0) indicates the transition point between the exponential and post-exponential growth phases.

FIG. 3, Panel C provides the transcription profiles of the spoIIIJ and yqjG genes. Time courses of the transcription of the spoIIIJ-lacZ and yqjG-lacZ gene fusions in *B. subtilis* ΔspoIIIJ (○) and *B. subtilis* ΔyqjG (■) were determined in cells growing at 37° C. in TY medium. β-galactosidase activities were determined in Units per $OD_{600}$. Zero time (t=0) indicates the transition point between the exponential and post-exponential growth phases.

FIG. 4 provides data showing that SpoIIIJ and YqjG are required for efficient protein secretion.

FIG. 4, Panel A provides results for precultures of *B. subtilis* ΔyqjG-IspoIIIJ and the parental strain *B. subtilis* 168, both transformed with plasmid pLip2031 (specifying LipA), pPSPPhoA5 (specifying PhoA), or pKTH10 (specifying AmyQ), prepared by overnight growth at 37° C. in TY medium containing 500 nM IPTG. Next, cells were washed with fresh TY medium without IPTG, diluted 20-fold in fresh TY medium containing 500 nM, 50 nM or no (0) IPTG, and incubated for 3 hours at 37° C. before sampling for SDS-PAGE and Western blotting. Specific antibodies were used to detect the cellular (pre-)LipA, PhoA, or (pre-)AmyQ levels (upper panels), and the levels of secreted LipA, PhoA, or AmyQ in the growth medium (lower panels). The positions of pre-LipA and pre-AmyQ (○), mature LipA, PhoA and AmyQ (●), or degradation products of PhoA (*) are indicated.

FIG. 4, Panel B provides data from experiments in which processing of pre-AmyQ in *B. subtilis* ΔyqjG-IspoIIIJ was analyzed by pulse-chase labeling at 37° C. in S7 medium with (500 nM; upper panel) or without (0) IPTG (lower panel), subsequent immunoprecipitation, SDS-PAGE, and fluorography. Cells were labeled with [35S]-methionine for 1 min prior to chase with excess non-radioactive methionine. Samples were withdrawn after the chase at the times indicated. Since the incorporation of label into (pre-)AmyQ cannot be stopped instantaneously by the addition of non-radioactive methionine, samples withdrawn at t=0, and t=1 contain lower amounts of labeled AmyQ than the sample withdrawn at t=5. The positions of pre-AmyQ (○) and mature AmyQ (●) are indicated.

FIG. 4, Panel C shows the translocation of pre-AmyQ-PSBT in SpoIIIJ-depleted cells lacking YqjG. To analyse pre-AmyQ translocation, cells of *B. subtilis* ΔyqjG-IspoIIIJ, *B. subtilis* DsecDF (positive control) and the parental strain *B. subtilis* 168 (negative control) were transformed with plasmid pKTH10-BT (specifying AmyQ-PSBT), and grown as described for Panel A. Cellular (biotinylated) AmyQ-PSBT was visualized by SDS-PAGE and Western blotting using AmyQ-specific antibodies (upper panel), or a streptavidin-HRP conjugate (lower panel). Precursor (○) and mature (●) forms of AmyQ-PSBT are indicated.

FIG. 6 provides illustrates that SpoIIIJ and YqjG are of minor importance for membrane protein biogenesis. Cells of *B. subtilis* ΔyqjG-IspoIIIJ xSecDF-Myc (ΔyqjG-IspoIIIJ) and the control strain *B. subtilis* xSecDF-Myc (parental), were grown overnight at 37° C. in TY medium containing 500 nM IPTG. Next, cells were washed with fresh TY medium without IPTG, diluted 20-fold in fresh TY medium containing 1% xylose (production SecDF-Myc) and 500 nM, 50 nM or no (0) IPTG, and incubated at 37° C. for 3 hours. Samples for SDS-PAGE and Western blotting were prepared from cells and specific antibodies were used to detect the cellular levels of SecDF-Myc, SipS, PrsA, FtsH, CtaC, and QoxA. The positions of the native proteins (●) and their degradation products (*) are indicated. Notably, FtsH-derived degradation products (FtsH, lower panel) were only visible after prolonged fluorography. Putative membrane topologies of these proteins are depicted (N, amino terminus; C, carboxyl-terminus; in, cytoplasmic side of the membrane; out, cell wall-exposed side of the membrane). In addition, this Figure indicates that the amino-termini of PrsA, CtaC and QoxA are lipid-modified.

FIG. 7 shows results of protease mapping of membrane proteins in SpoIIIJ-depleted cells lacking YqjG. To analyse the insertion of the membrane proteins SecDF-Myc, SipS, PrsA, FtsH, CtaC and QoxA, cells of *B. subtilis* ΔyqjG-IspoIIIJ xSecDF-Myc (ΔyqjG-IspoIIIJ) and the control strain *B. subtilis* xSecDF-Myc (parental), were grown overnight at 37° C. in TY medium containing 500 nM IPTG. Cells were washed with fresh TY medium without IPTG, diluted 20-fold in fresh TY medium without IPTG, and incubated at 37° C. for 3 hours. Next, the production of SecDF-Myc was induced by the addition of 1% xylose 15 min prior to protoplasting. Protoplasts were incubated for 30 min Without further additions, in the presence of trypsin (1 mg/ml), or trypsin and Triton X-100 (1%). This procedure was performed in parallel with cells of *B. subtilis* ΔyqjG-IspoIIIJ and *B. subtilis* 168 (parental), both containing pKTH10 for production of AmyQ. Samples were used for SDS-PAGE, Western blotting, and specific antibodies were used to detect SecDF-Myc, SipS, PrsA, FtsH, CtaC, QoxA, AmyQ or GroEL. The positions of intact proteins and pre-AmyQ (●), degradation products due to the incubation with trypsin (*), mature AmyQ (○), and trypsin-resistant fragments (▶) are indicated.

FIG. 8 provides data showing pulse-chase/protease mapping of membrane proteins in SpoIIIJ-depleted cells lacking YqjG. To analyse the kinetics of SipS, PrsA and QoxA insertion, cells of *B. subtilis* ΔyqjG-IspoIIIJ (ΔyqjG-IspoIIIJ) and the control strain *B. subtilis* 168 (parental) were grown at 37° C. in S7 medium, and labeled with [35S]-methionine for 1 min followed by a chase of 1 min with excess non-radioactive methionine. Cells were collected by centrifugation, and protoplast were subsequently prepared as described in the Examples. Protoplasts were incubated for 30 min without further additions, in the presence of trypsin (1 mg/ml), ortrypsin and Triton X-100 (1%) prior to immunoprecipitation, SDS-PAGE, and fluorography. Immunoprecipitation with anti-GroEL antibodies was used to check protoplast integrity. The positions of intact proteins (●) and trypsin-resistant fragments (▶) are indicated.

DESCRIPTION OF THE INVENTION

Figure 5A:
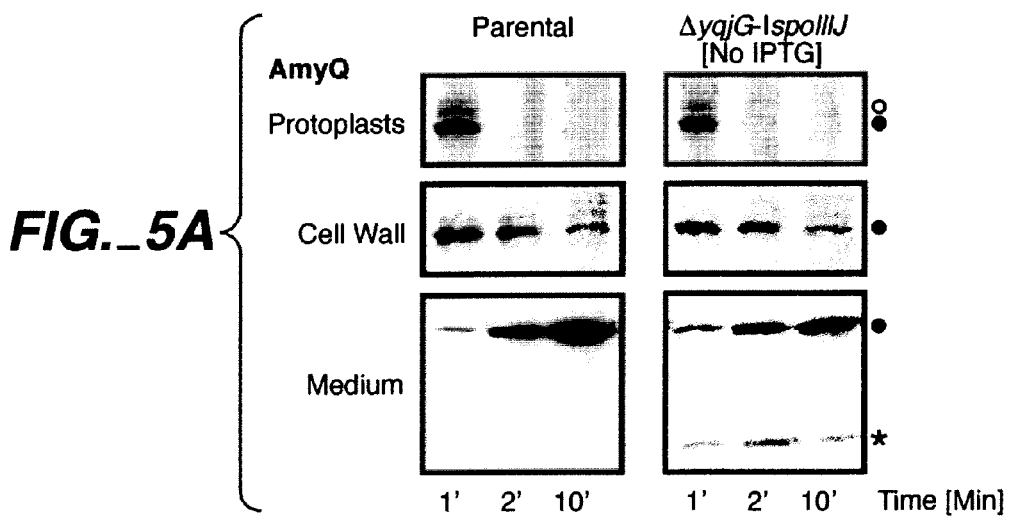
FIG. 5 provides data showing that SpoIIIJ and YqjG are required for efficient post- translocationally folding and release of secretory proteins. Processing and release of pre-AmyQ (Panel A), pre-pro-PhoA (Panel B), and pre-LipA (Panel C) were analyzed in *B. subtilis* ΔyqjG-IspoIIIJ and the parental strain *B. subtilis* 168 by pulse-chase labeling at 37° C. in S7 medium, subsequent cell fractionation (protoplasts, cell wall and medium), immunoprecipitation, SDS-PAGE, and fluorography. Cells were labeled with [$^{35}$S]-methionine for 1 min prior to chase with excess non-radioactive methionine. Samples were withdrawn at 1, 2, and 10 min after the chase. Cells and medium were separated by centrifugation, and protoplasts were subsequently prepared as described in the Examples. Finally, the cell wall and protoplast fractions were separated by centrifugation. The positions of pre-AmyQ and pre-pro-PhoA (○), degradation products of (pro-) PhoA and AmyQ (*) and mature AmyQ, PhoA and. LipA (●) are indicated.

The present invention provides methods and compositions for the efficient secretion of proteins from Gram-positive microorganisms. All patents and publications, including all sequences disclosed within such patents and publications, referred to herein are expressly incorporated by reference.

Definitions

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, N.Y. (1991) provide one of skill with a general dictionary of many of the terms used in this invention. Although any methods and materials similar or equivalent to those described herein can be used in the practice or testing of the present invention, the preferred methods and materials are described. Numeric ranges are inclusive of the numbers defining the range. Unless otherwise indicated, nucleic acids are written left to right in 5' to 3' orientation; amino acid sequences are written left to right in amino to carboxy orientation, respectively. It is to be understood that this invention is not limited to the particular methodology, protocols, and reagents described, as these may vary.

The headings provided herein are not limitations of the various aspects or embodiments of the invention which can be had by reference to the specification as a whole. Accordingly, the terms defined immediately below are more fully defined by reference to the specification as a whole.

As used herein, the term "host cell" refers to a cell that has the capacity to act as a host and expression vehicle for an expression cassette according to the invention. In one embodiment, the host cell is a Gram-positive microorganism. In a preferred embodiment according to the present invention, "host cell" refers to members of the genus *Bacillus*. As used herein, the genus *Bacillus* includes all members known to those of skill in the art, including but not limited to *B. subtilis*, *B. licheniformis*, *B. lentus*, *B. brevis*, *B. stearothermophilus*, *B. alkalophilus*, *B. amyloliquefaciens*, *B. coagulans*, *B. circulans*, *B. lautus*, *B. clausii*, and *B. thuringiensis*.

As used herein, the term "polypeptide" refers to a compound made up of amino acid residues linked by peptide bonds. The term "protein" as used herein may be synonymous with the term "polypeptide" or may refer, in addition, to a complex of two or more polypeptides.

As used herein, the terms "protein of interest" and "polypeptide of interest" refer to the protein to be expressed and secreted by the host cell. The protein of interest may be any protein that up until now has been considered for expression in prokaryotes. The protein of interest may be either homologous or heterologous to the host.

As used herein, the terms "chimeric polypeptide" and "fusion polypeptide" are used interchangeably in reference to a protein that comprises at least two separate and distinct regions that may or may not originate from the same protein. For example, a signal peptide linked to the protein of interest wherein the signal peptide is not normally associated with the protein of interest would be termed a chimeric polypeptide or chimeric protein.

As used herein, the terms "signal peptide" and "signal sequence" refer to an amino-terminal extension on a protein to be secreted. Nearly all secreted proteins use an amino-terminal protein extension which plays a crucial role in the targeting to and translocation of precursor proteins across the membrane and which is proteolytically removed by a signal peptidase during or immediately following membrane transfer. In preferred embodiments of the present invention, the signal sequence is the sec-dependent signal peptides derived from *Bacillus*.

As used herein, the term "enhanced" refers to improved production of proteins of interest. In preferred embodiments, the present invention provides enhanced (i.e., improved) production and secretion of a protein of interest. In these embodiments, the "enhanced" production is improved as compared to the normal levels of production by the host (e.g., wild-type cells). Thus, for heterologous proteins, basically any expression is enhanced, as the cells normally do not produce the protein.

As used herein, the terms "isolated" and "purified" refer to a nucleic acid or amino acid that is removed from at least one component with which it is naturally associated.

As used herein, the term "heterologous protein" refers to a protein or polypeptide that does not naturally occur in a host cell. Examples of heterologous proteins include enzymes such as hydrolases including proteases, cellulases, amylases, other carbohydrases, and lipases; isomerases such as racemases, epimerases, tautomerases, or mutases; transferases, kinases and phosphatases, hormones, growth factors, cytokines, antibodies and the like.

A "heterologous" nucleic acid construct or sequence has a portion of the sequence that is not native to the cell in which it is expressed. "Heterologous," with respect to a control sequence refers to a control sequence (i.e. promoter or enhancer) that does not function in nature to regulate the same gene the expression of which it is currently regulating. Generally, heterologous nucleic acid sequences are not endogenous to the cell or part of the genome in which they are present, and have been added to the cell, by infection, transfection, microinjection, electroporation, or the like. In some embodiments, "heterologous" nucleic acid constructs contain a control sequence/DNA coding sequence combination that is the same as, or different from a control sequence/DNA coding sequence combination found in the native cell.

As used herein, the term "homologous protein" refers to a protein or polypeptide native or naturally occurring in a host cell. The present invention encompasses host cells producing the homologous protein via recombinant DNA technology. The present invention further encompasses a host cell which may have one or more deletions or one or more interruptions of the nucleic acid encoding the naturally occurring homologous protein or proteins, such as, for example, a protease, and having nucleic acid encoding the homologous protein or proteins re-introduced in a recombinant form (i.e., in an expression cassette). In other embodiments, the host cell produces the homologous protein.

As used herein, the term "nucleic acid molecule" includes RNA, DNA and cDNA molecules. It will be understood that, as a result of the degeneracy of the genetic code, a multitude of nucleotide sequences encoding a given protein may be produced.

As used herein, the term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

As used herein, the terms "expression cassette" and "expression vector" refer to a nucleic acid construct generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter.

As used herein, the term "plasmid" refers to a circular double-stranded (ds) DNA construct used as a cloning vector, and which forms an extrachromosomal self-replicating genetic element in many bacteria and some eukaryotes.

As used herein, the term "selectable marker-encoding nucleotide sequence" refers to a nucleotide sequence which is capable of expression in the host cells and where expression of the selectable marker confers to cells containing the expressed gene the ability to grow in the presence of a corresponding selective agent or lack of an essential nutrient.

As used herein, the term "promoter" refers to a nucleic acid sequence that functions to direct transcription of a downstream gene. In preferred embodiments, the promoter is appropriate to the host cell in which the target gene is being expressed. The promoter, together with other transcriptional and translational regulatory nucleic acid sequences (also termed "control sequences") is necessary to express a given gene. In general, the transcriptional and translational regulatory sequences include, but are not limited to, promoter sequences, ribosomal binding sites, transcriptional start and stop sequences, translational start and stop sequences, and enhancer or activator sequences.

As used herein, "chimeric gene" and "heterologous nucleic acid construct" refer to a non-native gene (i.e., one that has been introduced into a host) that may be composed of parts of different genes, including regulatory elements. A chimeric gene construct for transformation of a host cell is typically composed of a transcriptional regulatory region (promoter) operably linked to a heterologous protein coding sequence, or, in a selectable marker chimeric gene, to a selectable marker gene encoding a protein conferring antibiotic resistance or other selectable properties to transformed cells. A typical chimeric gene of the present invention, for transformation into a host cell, includes a transcriptional regulatory region that is constitutive or inducible, a signal peptide coding sequence, a protein coding sequence, and a terminator sequence. In some embodiments, chimeric gene constructs also include a second DNA sequence encoding a signal peptide if secretion of the target protein is desired.

A nucleic acid is "operably linked" when it is placed into a functional relationship with another nucleic acid sequence. For example, DNA encoding a secretory leader, i.e., a signal peptide, is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the term "gene" means the segment of DNA involved in producing a polypeptide chain, that may or may not include regions preceding and following the coding region (e.g. 5' untranslated (5' UTR) or "leader" sequences and 3' UTR or "trailer" sequences), as well as intervening sequences (introns) between individual coding segments (exons).

In some embodiments, the gene encodes therapeutically significant proteins or peptides, such as growth factors, cytokines, ligands, receptors and inhibitors, as well as vaccines and antibodies. The gene may encode commercially important industrial proteins or peptides, such as enzymes (e.g., proteases, carbohydrases such as amylases and glucoamylases, cellulases, oxidases and lipases). However, it is not intended that the present invention be limited to any particular enzyme or protein. In some embodiments, the gene of interest is a naturally-occurring gene, a mutated gene or a synthetic gene.

A nucleic acid sequence is considered to be "selectively hybridizable" to a reference nucleic acid sequence if the two sequences specifically hybridize to one is another under moderate to high stringency hybridization and wash conditions. Hybridization conditions are based on the melting temperature I of the nucleic acid binding complex or probe. For example, "maximum stringency" typically occurs at about Tm-5° C. (5° below the Tm of the probe); "high stringency" at about 5-10° C. below the Tm; "intermediate stringency" at about 10-20° C. below the Tm of the probe; and "low stringency" at about 20-25° C. below the Tm. Functionally, maximum stringency conditions may be used to identify sequences having strict identity or near-strict identity with the hybridization probe; while high stringency conditions are used to identify sequences having about 80% or more sequence identity with the probe.

Moderate and high stringency hybridization conditions are well known in the art. An example of high stringency conditions includes hybridization at about 42° C. in 50% formamide, 5×SSC, 5× Denhardt's solution, 0.5% SDS and 100 μg/ml denatured carrier DNA followed by washing two times in 2×SSC and 0.5% SDS at room temperature and two additional times in 0.1×SSC and 0.5% SDS at 42° C.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention. "Recombination, "recombining," or generating a "recombined" nucleic acid is generally the assembly of two or more nucleic acid fragments wherein the assembly gives rise to a chimeric gene.

As used herein, the terms "transformed," "stably transformed," and "transgenic" used in reference to a cell means the cell has a non-native (heterologous) nucleic acid sequence integrated into its genome or as an episomal plasmid that is maintained through two or more generations.

As used herein, the term "expression" refers to the process by which a polypeptide is produced based on the nucleic acid sequence of a gene. The process includes both transcription and translation.

As used herein, the term "introduced" used in the context of inserting a nucleic acid sequence into a cell, means "transfection," "transformation," or "transduction," and includes reference to the incorporation of a nucleic acid sequence into a eukaryotic or prokaryotic cell where the nucleic acid sequence may be incorporated into the genome of the cell (e.g., chromosome, plasmid, plastid, or mitochondrial DNA), converted into an autonomous replicon, or transiently expressed (for example, transfected mRNA).

In one embodiment, present invention finds use in enhancing the secretion of any protein of Interest that may be made to be secreted via the Sec-dependent secretion pathway. Any protein of interest that may be fused to a Sec-dependent signal peptide by recombinant DNA methods finds use in the present invention.

In particularly preferred embodiments of the present invention, the host cell is rendered capable of enhanced secretion of a protein of interest. In some embodiments, the protein of interest is endogenous, while in alternative embodiments, it is heterologous. In further embodiments, the protein of interest is a chimeric protein, in that the native protein of interest is fused to a Sec-dependent signal sequence. In additional embodiments, the host cell is also transformed with a DNA construct encoding the spoIIIJ gene. In some preferred embodiments, the spoIIIJ gene is operably linked to a promoter. In some embodiments, the promoter is constitutive, while in other embodiments, it is inducible. One preferred promoter is the Pspac.

It is contemplated that by varying the level of induction of an inducible promoter that it may be possible to modulate the expression of the spoIIIJ gene product and thereby modulate the secretion of the protein of interest. It is also contemplated that a host cell deficient in the spoIIIJ gene may have impaired protein secretion.

In preferred embodiments of the present invention, the host cell is a Gram-positive cell. In particularly preferred embodiments, the Gram-positive cell is a member of the genus *Bacillus*.

DETAILED DESCRIPTION OF THE INVENTION

Prior to the development of the present invention, an unexplained observation was that *B. subtilis* cells lacking SPase II accumulated significantly increased levels of pre-AmyQ (Tjalsma et al., [1999], supra). As the latter effect was never observed in prsA mutant strains (Kontinen and Sarvas, Mol. Microbiol., 8:727-737 [1993]; and Jacobs et al., Mol. Microbiol., 8:957-966 [1993]), it was concluded that the increased pre-AmyQ accumulation in Isp mutant strains was due to the malfunction of one or more lipoproteins other than PrsA. This resulted in the development of the present invention in which lipoproteins of *B. subtilis* with previously unknown roles in protein secretion are provided.

During the development of the present invention, the amino acid sequences of all 114 (predicted) lipoproteins of *B. subtilis* (Tjalsma et a., [1999], supra) were used for similarity searches in public databases. Strikingly, the predicted lipoproteins SpoIIIJ and YqjG both showed significant similarity to the Oxa1 protein of yeast mitochondria (See, FIG. 1). This inner membrane protein has been implicated in the export of the amino- and carboxyl-termini of the mitochondrially-encoded precursor of cytochrome c oxidase subunit II (pre-CoxII) from the mitochondrial matrix (Hell et al., FEBS Lett., 418:367-370 [1997]; and Hell et al., Proc. Natl. Acad. Sci. USA 95:2250-2255 [1998]). In addition, it was recently shown that the *E. coli* orthologue of Oxa1p, denoted YidC, is associated with the Sec translocase (Scotti et al., EMBO J., 19:542-549 [2000]). However, Samuelson and co-workers (Samuelson et al., Nature 406:637-641 [2000]) demonstrated that YidC of *E. coli* is of major importance for the biogenesis of several membrane proteins, whereas the export of secretory proteins was hardly impaired in YidC-depleted cells.

Despite the differences in the roles of SpoIIIJ and YqjG in protein expression among various organisms, the present invention provides the identification of roles of SpoIIIJ and YqjG in protein secretion and/or membrane protein biogenesis. Indeed, results obtained during the development of the present invention show that SpoIIIJ and YqjG are important for post-translocational stages in protein secretion. Consistent with an important role in secretion, the presence of at least one of these two Oxa1p orthologues is essential for cell growth. It is noted that under SpoIIIJ- and YqjG-limiting conditions that strongly affect protein secretion, the stability of various membrane proteins is not, or only very mildly, affected. Also, while SpoIIIJ is essential for sporulation (Errington et al., J. Gen. Microbiol., 138:2609-2618 [1992]), its paralogue YqjG is not involved in this developmental process. Taken together, these data indicate that SpoIIIJ and YqjG have acquired functions that are at least partly different from those of other members of the Oxa1 family.

Recently, the yidC gene of *E. coli*, specifying a SpoIIIJ/YqjG orthologue (FIG. 1), was shown to be essential for cell viability (See, Samuelson et al., supra). In contrast, the spoIIIJ gene of *B. subtilis* is not essential for growth. In fact, spoIIIJ was originally identified as the gene containing the spo-87 mutation that blocks sporulation of *B. subtilis* cells at stage III, after the completion of prespore engulfment (Errington et al., supra). To search for possible functions of the YqjG protein, a yqjG disruption strain was constructed with the integration vector pMutin2 (See, FIG. 2). The fact that *B. subtilis* ΔyqjG could be obtained showed that YqjG, like SpoIIIJ, is not essential for growth (See, FIG. 3, Panel A). Notably, disruption of the yqjG gene did not detectably affect sporulation, while a ΔspoIIIJ control strain constructed with pMutin2 was unable to develop viable spores (data not shown). Thus, as discussed in greater detail in the Experimental section, YqjG has no essential function in the sporulation process, in contrast to SpoIIIJ.

As indicated above, proteins homologous to Oxa1p are conserved in eubacteria and eukaryotic organelles, where they appear to have important functions in protein transport and membrane assembly. In fact, SpoIIIJ of *B. subtilis* was the first protein of this family to which a function was assigned. Errington and co-workers (Errington et al., supra) reported that a spoIIIJ mutation blocks sporulation of *B. subtilis* cells at stage III, after the completion of forespore engulfment. It was thought that this protein was involved in a signal transduction pathway, coupling gene expression in the forespore to concomitant events in the mother cell. However, the exact function of SpoIIIJ in sporulation was not unraveled.

During the development of the present invention, it was determined that the synthesis of either SpoIIIJ, or its paralogue YqjG, is required for growth of the Gram-positive eubacterium *B. subtilis*. Furthermore, as discussed in greater detail below, the secretion of the mature AmyQ, PhoA and LipA proteins into the growth medium was strongly impaired under conditions of SpoIIIJ/YqjG-limitation. Notably, the reduction in AmyQ levels in the medium was not paralleled by reduced rates of pre-AmyQ translocation and processing, or the cellular accumulation of pre-AmyQ, as previously documented for secDF, tepA or sip mutant strains with translocation defects (Bolhuis et al., [1998], supra; Tjalsma et al., [1998], supra; Bolhuis et al., [1999a], supra; and Tjalsma et al., J. Biol. Chem., 272:25983-25992 [1997]). Pulse-chase experiments combined with cell fractionation showed that degradation of AmyQ and PhoA occurs in the membrane-cell wall interface soon after the proteins have left the translocation channel (See, FIG. 7). Thus, the secretion defect observed with SpoIIIJ-depleted cells lacking YqjG occurs in the post-translocational stages that involve the folding of secretory proteins into their active and protease-resistant conformation. The latter is of particular importance because the extracytoplasmic side of the membrane, the cell wall and the growth medium of *B. subtilis* are highly proteolytic (Tjalsma et al., [2000a], supra; and Antelmann et al., Genome Res., 11:1484-1502 [2001]). In a wild-type cell, it is contemplated that SpoIIIJ and YqjG facilitate the folding of translocated proteins in at least two different ways. However, it is not intended that the present invention be limited to any particular mechanism. Nonetheless, it is conceivable that SpoIIIJ and YqjG have a direct role in the correct folding of mature proteins shortly after their translocation across the membrane, similar to the essential function proposed for the folding catalyst PrsA (Tjalsma et al., [1999], supra; and Kontinen et al., supra). Alternatively, it is contemplated that SpoIIIJ and YqjG have an indirect role in protein secretion by modulating the activity of folding catalysts, such as PrsA. The fact that SpoIIIJ-depleted cells lacking YqjG do not accumulate increased levels of the precursor form of AmyQ, as previously observed in cells lacking SPase II, indicates that the typical lipoproteins SpoIIIJ and YqjG are not responsible for the accumulation of pre-AmyQ in SPase II mutant cells. Thus, unprocessed lipoproteins other than SpoIIIJ and YqjG must be responsible for the latter phenomenon, unless the secretion defects caused by impaired pre-SpoIIIJ and pre-YqjG processing in the absence of SPase II are different from those caused by SpoIIIJ/YqjG limitation. However, as indicated above, it is not intended that the present invention be limited to any particular or specific mechanism.

In recent years, the Oxa1p protein of yeast mitochondria was shown to be required for the processing of mitochondrially-encoded precursors (Bauer et al., Mol. Gen. Genet., 245: 272-278 [1994]), the export of amino- and carboxyl-termini from pre-Cox II synthesized in the mitochondrial matrix (Hell et al., [1997], supra; and Hell et al., [1998], supra) and the insertion of transmembrane domains into the mitochondrial inner membrane in a pairwise fashion (Herrmann et al., EMBO J., 16:2217-2226 [1997]). Taking into consideration the fact that yeast mitochondria completely lack Sec components, and that the Oxa1p orthologue in chloroplasts (Albino III) is required for the Sec-independent integration of the light-harvesting chlorophyll-binding protein into the thylakoid membrane (Moore et al., J. Biol. Chem., 275:1529-1532 [2000]), it is contemplated that members of the Oxa1p family represent the key components of a novel pathway for protein export or membrane protein assembly (Stuart and Neupert, Nature 406:575-577 [2000]). Consistent with this view, YidC of *E. coli* was shown to facilitate the Sec-independent insertion of certain membrane proteins, such as the M13 procoat, being of minor importance for the export of Sec-dependent pre-proteins (Samuelson et al., supra). Nevertheless, YidC, was also shown to be associated with the Sec machinery, indicating that this protein has a more general role in membrane protein biogenesis in *E. coli*, for example by catalyzing the exit of membrane proteins from the Sec translocase (Scotti et al., supra; Samuelson et al., supra; and Houben et al., FEBS Lett., 476:229-233 [2000]). Indications for such a lateral movement were obtained by Urbanus and co-workers (Urbanus et al., EMBO Rep., 2:524-529 [2001]), who demonstrated a sequential interaction of the membrane protein FtsQ with SecY and YidC. Recent studies by Houben et al. (Houben et al., J. Biol. Chem., 277:35880-35886 [2002]) showed that YidC has the ability to contact a transmembrane domain very early during biogenesis, when it is not even fully exposed outside the ribosome. Thus, it is contemplated that YidC has a role in both the reception and lipid partitioning of transmembrane segments. The results obtained during the development of the present invention indicate that the essential function of SpoIIIJ and YqjG in *B. subtilis* relates to a general role in protein secretion. However, it is not intended that the present invention be limited to any particular or specific mechanism.

The results obtained during the development of the present invention support the view that these proteins are not involved in the actual membrane insertion and translocation of secretory pre-proteins. Furthermore, the stability of the membrane proteins FtsH and CtaC is affected under conditions of SpoIIIJ/YqjG limitation. However, pulse-chase/protease mapping experiments showed that the insertion kinetics of PrsA SipS and QoxA were not significantly affected after chase of a 1-min under these conditions. It should be noted that the membrane topology of QoxA is similar to that of Lep of *E. coli*, of which the insertion was significantly affected after a 2-min chase in YidC-depleted cells (See, Samuelson et al., supra). Although, pulse-chase experiments could not be performed with SecDF-Myc, CtaC, and FtsH to monitor the kinetics of membrane insertion under conditions of SpoIIIJ/YqjG-depletion, it is contemplated that the defect on the post-translocational folding of secretory proteins is the most prominent effect of SpoIIIJ/YqjG depletion in *B. subtilis*. Thus, results obtained during the development of the present invention, taken together with the well-documented requirement of Oxa1p and YidC for membrane protein biogenesis, indicate that SpoIIIJ and YqjG have specific roles in membrane protein biogenesis in *B. subtilis*. Thus, it is contemplated that different orthologous members of the Oxa1 protein family have acquired different species or genus-specific functions in Sec-dependent and Sec-independent membrane protein biogenesis and protein secretion. Interestingly, not only orthologous Oxa1-like proteins, but also Oxa1-like paralogues within one organism have acquired (partly) distinct functions, as evidenced by the present observation that SpoIIIJ, but not YqjG, is required for spore development. Similarly, only one of the two Oxa1p orthologues of *Schizosaccharomyces pombe* is essential for respiration (Bonnefoy et al., Mol. Microbiol., 35:1135-1145 [2000]). As only minor differences in the timing of transcription have been observed for the genes specifying the paralogous Oxa1p proteins of *B. subtilis* (See, FIG. 3, Panel C) and *S. pombe* (See, Bonnefoy et al., [2000], supra), the differences in function of these protein pairs are, most likely, based on differences in their primary structures.

As SpoIIIJ and YqjG are important for post-translocational protein folding steps in the secretion process, it is contemplated that SpoIIIJ is specifically required is for the folding of certain, translocated sporulation factors. The importance of protein transport for sporulation is underscored by the observations that SecA, and the type I SPases, SipT and SipV, are required for this process, as indicated by results obtained during the development of the present invention and data included in various reports (Bonnefoy et al., [2000], supra; Jiang et al., J. Bacteriol., 182:303-310 [2000]). In addition, it is contemplated that SpoIIIJ is involved in the insertion of specific membrane proteins that are essential for the sporulation process after stage III. It is further contemplated that these membrane proteins are involved in the communication between the forespore and the mother cell. However, as indicated above, it is not intended that the present invention be limited to any particular or specific mechanism.

EXPERIMENTAL

The following examples serve to illustrate certain preferred embodiments and aspects of the present invention and are not to be construed as limiting the scope thereof.

In the experimental disclosure which follows, the following abbreviations apply: eq (equivalents); M (Molar); µM (micromolar); N (Normal); mol (moles); mmol (millimoles); µmol (micromoles); nmol (nanomoles); g (grams); mg (milligrams); kg (kilograms); µg (micrograms); L (liters); ml (milliliters); µl (microliters); cm (centimeters); mm (millimeters); µm (micrometers); nm (nanometers); ° C. (degrees Centigrade); h (hours); min (minutes); sec (seconds); msec (milliseconds); Ci (Curies) mCi (milliCuries); µCi (microCuries); TLC (thin layer achromatography); Ts (tosyl); Bn (benzyl); Ph (phenyl); Ms (mesyl); Et (ethyl), Me (methyl); SPase (signal peptidase); Ap (ampicillin); Cm (chloramphenicol); Em (erythromycin); HRP (horseradish peroxidase); IPTG (isopropyl-β-D-thiogalacto-pyranoside); Km (kanamycin); OD (optical density); PAGE (polyacrylamide gel electrophoresis); SDS-PAGE (sodium dodecyl sulfate polyacrylamide gel electrophoresis); PCR (polymerase chain reaction); RBS (ribosome binding site); Tc (tetracycline); TY (tryptone/yeast extract); Roche (Roche Molecular Biochemicals, Roche Diagnostics, Indianapolis, Ind.); Millipore (Millipore Corp., Bedford, Mass.); Amersham (Amersham Biosciences, Piscataway, N.J.); Clontech (BD Clontech, Palo Alto, Calif.); Sigma (Sigma Aldrich, St. Louis, Mo.).

EXAMPLE 1

Plasmids, Bacterial Strains, Media and Assay Systems

Table I lists the plasmids and bacterial strains used. TY medium (tryptone/yeast extract) contained Bacto tryptone (1%), Bacto yeast extract (0.5%) and NaCl (1%). Minimal medium for *B. subtilis* was prepared as described by Tjalsma et al. ([1998], supra). Schaeffer's sporulation medium (SSM) was prepared as described by Schaeffer et al., (Schaeffer et al., Proc. Natl. Acad Sci. USA 54:704-711 [1965]). When required, medium for *E. coli* was supplemented with kanamycin (Km; 40 µg/ml), ampicillin (Ap; 50 µg/ml), or erythromycin (Em; 100 µg/ml); media for *B. subtilis* were supplemented with chloramphenicol (Cm; 5 µg/ml), Km (10 µ/ml), tetracycline (Tc; 6 µg/ml), or Em (1 µg/ml).

The pMutin2 plasmid was described by Vagner et al., (Vagner et al., Microbiol., 144:3097-3104 [1998]), while the pUK21 plasmid was described by Vieria and Messing (Vieria and Messing, Gene 100:189-194 [1990]), pLip2031 was described by Dartois et al. (Dartois et al., Appl. Environ. Microbiol., 60:1670-1673 [1994]), pKTH10 was described by Palva (Palva, Gene 19:81-87 [1982]), and pKTH10-BT was described by Tjalsma et al., (Tjalsma et al., [1998], supra).

The *E. coli* MC1061 strain was described by Wertman et al (Wertman et al., Genen., 49:253-262 [1986]), while the *B. subtilis* 168 strain was described by Kunst et al. (Kunst et al., Nature 390:249-256 [1997]), the *B. subtilis* ΔsecDF and xSecDF-Myc strains were described by Bolhuis et al. (Bolhuis et al., J. Biol. Chem., 273:21217-21224 [1998]).

TABLE I

Plasmids and Bacterial Strains
Relevant Properties

| Plasmids | |
| --- | --- |
| pMutin2 | pBR322-based integration vector for *B. subtilis*; contains a multiple cloning site downstream of the Pspac promoter, and a promoter-less lacZ gene preceded by the RBS of the spoVG gene; Ap$^r$; Em$^r$ |
| pMutin-ΔspoIIIJ | As pMutin2, contains an internal fragment of the *B. subtilis* spoIIIJ gene |
| pMutin-IspoIIIJ | As pMutin2, contains the 5' part of the *B. subtilis* spoIIIJ gene |
| pMutin-ΔyqjG | As pMutin2, contains an internal fragment of the *B. subtilis* yqjG gene |
| pUK21 | Cloning vector; 2.8 kb; Km$^r$ |
| pUKyqjG-Tc | pUK21 derivative for the disruption of yqjG; Km$^r$; Tc$^r$ |
| pPSPPhoA5 | Plasmid carrying *E. coli* phoA gene fused to the prepro region of the lipase gene from *Staphylococcus hyicus*; Cm$^r$ |
| pLip2031 | Encodes LipA from *B. subtilis* Km$^r$ |
| pKTH10 | Encodes AmyQ of *Bacillus amyloliquefaciens*; Km$^r$ |
| pKTH10-BT | As pKTH10, encodes the AmyQ-PSBT fusion protein |
| Strains | |
| *E. coli* | |
| MC1061 | F$^-$; araD139; Δ (ara-leu)7696; Δ (lac)X74; galU; galK; hsdR2; mcrA; mcrB1; rspL |
| *B. subtilis* | |
| 168 | trpC2 |
| ΔspoIIIJ | Derivative of 168; contains an integrated copy of plasmid pMutin2 in the spoIIIJ gene; spoIIIJ-lacZ, Em$^r$ |
| ΔyqjG | Derivative of 168; contains an integrated copy of plasmid pMutin2 in the yqjG gene; yqjG-lacZ, Em$^r$ |

TABLE I-continued

Plasmids and Bacterial Strains
Relevant Properties

| | |
|---|---|
| yqjG-Tc | Derivative of 168; 5' part of the yqjG gene is replaced with a phosphatases resistance marker, using pUKyqjG-Tc, by double cross-over recombination; yqjG::Tc, Tc$^r$ |
| ΔyqjG-IspoIIIJ | Derivative of *B. subtilis* 168 yqjG-Tc; contains an integrated copy of plasmid pMutin2 in the spoIIIJ region; Pspac-spoIIIJ, spoIIIJ-lacZ, Em$^r$; IPTG-inducible spoIIIJ transcription; Tc$^r$; Em$^r$ |
| ΔsecDF | Originally referred to as MIF; derivative of *B. subtilis* 168; contains an integrated copy of plasmid pMutin2 in the secDF gene; secDF-lacZ, Em$^r$ |
| xSecDF-Myc | Derivative of *B. subtilis* 168; amyE::xylA-secDFmyc; Cm$^r$; also referred to as XDF-Myc |

Assay for Spore Development

The efficiency of sporulation was determined by overnight growth in SSM medium, killing of cells with 0.1 volume chloroform, and subsequent plating.

Beta-Galactosidase Activity Assay

Overnight cultures were diluted 100-fold in fresh medium and samples were taken at hourly intervals for optical density (OD) readings and β-galactosidase activity determinations. The assays and the calculations of β-galactosidase units (expressed as units per OD$_{600}$) were carried out as known in the art (See e.g., Miller, *Experiments in Molecular Genetics*, Cold Spring Harbor Laboratory Press, New York [1982]).

Western Blot Analysis and Immunodetection

Western blotting was performed as known in the art (See e.g., Kyhse-Andersen, J. Biochem. Biophys. Meth., 10:203-209 (19841). After separation by SDS-PAGE, proteins were transferred to Immobilon-PVDF membranes (Millipore). To detect LipA, PhoA, AmyQ(-PSBT), carboxyl-terminally Myc-tagged SecDF, SipS, PrsA, FtsH, CtaC or QoxA, *B. subtilis* cells were separated from the growth medium. Cells were resuspended in lysis buffer (20 mM potassium phosphate, pH 7.5; 15 mM MgCl$_2$; 20% sucrose; 0.5 mg/ml lysozyme) and incubated for 15 min at 37° C. Next, 1 volume of SDS sample buffer (100 mM Tris-HCl [pH 6]; 4% SDS; 10% 2-mercaptoethanol; 30% glycerol; 0.005% bromophenolblue; and 1% Triton X-100) was added and the incubation was prolonged for 15 min at 37° C. in the presence of Complete™ protease inhibitors (Roche). In general, proteins were visualized with the ECL detection system, using rabbit/mouse sera and horseradish peroxidase (HRP)-anti-rabbit/mouse-IgG conjugates (Amersham). Carboxyl-terminally Myc-tagged SecDF was visualized with monoclonal c-Myc antibodies (Clontech), and biotinylated AmyQ-PSBT was visualized with a streptavidin-HRP conjugate (Amersham).

Protein Labeling, Immunoprecipitation, SDS-PAGE and Fluorography

*B. subtilis* ΔyqjG-IspoIIIJ was grown overnight in S7 medium (See, van Dijl et al., J. Gen. Microbiol., 137:2073-2083 [1991a]) supplemented with 500 nM IPTG, Em (1 μg/ml) and Tc (6 μ/ml). Cells were washed with fresh S7 medium without IPTG and diluted 1:10 in fresh S7 medium containing Em (1 μ/ml), in the presence or absence of IPTG. After 2 hours of growth, cells were resuspended in methionine and cysteine-free S7 (S7 starvation) medium with or without IPTG and grown for another hour prior to pulse-chase labeling. Immunoprecipitation, SDS-PAGE and fluorography were performed as known in the art (See, van Dijl et al., Mol. Gen. Genet., 227:4048 [1991b]; and van Dijl et al., [1991a], supra).

Protease Accessibility

Protoplasts were prepared from late exponentially growing cells of *B. subtilis*. Cells were resuspended in protoplast buffer (20 mM potassium phosphate, pH 7.5; 15 mM MgCl$_2$; 20% sucrose) and incubated for 30 min with 1 mg/ml lysozyme (37 C). Protoplasts were collected by centrifugation, resuspended in fresh protoplast buffer and incubated at 37° C. in the presence of 1 mg/ml trypsin (Sigma) for 30 min. The reaction was terminated by the addition of Complete™ protease inhibitors (Roche) and protoplasts were used for SDS-PAGE and Western-blotting. In parallel, protoplasts were incubated without trypsin, or in the presence of trypsin and 1% Triton X-100.

EXAMPLE 2

DNA Techniques

Procedures for DNA purification, restriction, ligation, agarose gel electrophoresis, and transformation of *E. coli* were carried out as known in the art (See e.g., Sambrook et al. *Molecular Cloning: A Laboratory Manual*, Cold Spring Harbor, N.Y. [1989]). Enzymes were obtained from Roche. *B. subtilis* was transformed as known in the art (See, Tjalsma et al., [1998], supra). PCR was carried out with Pwo DNA polymerase (Roche), as known in the art (See, van Dijl et al J. Biol. Chem., 270:3611-3618 [1995]). The BLAST algorithm (See, Altschul et al., Nucl. Acids Res., 25:3389-3402 [1997]) was used for protein comparisons in GenBank.

To construct *B. subtilis* ΔspoIIIJ, an internal fragment of the spoIIIJ gene was amplified with the primers spoIIIJ-1 (5'-GAG AAT TCG ACG GGA GAT AAC TAC GGG C-3'; SEQ ID NO:1) and spoIIIJ-2 (5'-ATG GAT CCT ATG CTC TGA AAT CGC CTG GG-3'; SEQ ID NO:2). The amplified fragment was cleaved with EcoRI and BamHI, and ligated into the corresponding sites of pMutin2, resulting in pMutin-ΔspoIIIJ. Next, *B. subtilis* ΔspoIIIJ was obtained by a single cross-over (Campbell-type) integration of pMutin-ΔspoIIIJ into the spoIIIJ gene of *B. subtilis* 168, in such a way that the spoIIIJ gene was disrupted and the spoVG-lacZ reporter gene of pMutin2 was placed under the transcriptional control of the spoIIIJ promoter region (See, FIG. 2). Simultaneously, the jag gene located downstream of spoIIIJ was placed under the control of the isopropyl-β-D-thiogalacto-pyranoside (IPTG)-dependent Pspac promoter (See, FIG. 2).

To construct *B. subtilis* ΔyqjG, an internal fragment of the yqjG gene was amplified with the primers yqjG-3 (5'-TGA AGC TTG CCG GGC TGT TTC ACG G-3'; SEQ ID NO:3) and yqjG-2 (5'-ATG GAT CCA TCG TCA TCA TCA CAG GGA AGA TG-3'; SEQ ID NO:4). The amplified fragment was cleaved with HindIII and BamHI, and ligated into the corresponding sites of pMutin2, resulting in pMutin-ΔyqjG. Next, *B. subtilis* ΔyqjG was obtained by a single cross-over integration of pMutin-ΔyqjG into the yqjG gene of *B. subtilis* 168, in such a way that the yqjG gene was disrupted and the spoVG-lacZ reporter gene of pMutin2 was placed under the transcriptional control of the yqjG promoter region (See, FIG. 2).

To construct *B. subtilis* ΔyqjG-IspoIIIJ, a fragment comprising the yqjG gene and upstream and downstream sequences was first amplified with the primers yqjG-1 (5'-GCT TTG GAT TTC TTT TGC CGT CTC-3'; SEQ ID NO:5) and yqjG-4 (5'-GGT TCG TGA GCA TAA AGG GM GC-3'; SEQ ID NO:6). The amplified fragment was cleaved with XbaI and KpnI, and ligated into the corresponding sites of pUK21. Next, the 714 bp EcoRI and PstI fragment, containing the 5' sequences of the yqjG gene, was replaced with a tetracycline resistance marker resulting in plasmid pUKyqjG-Tc. Next, the chromosomal yqjG gene of *B. subtilis* 168 was largely deleted by a double cross-over recombination event with linearized pUKyqjG-Tc, resulting in *B. subtilis* yqjG-Tc (See, FIG. 2).

To construct *B. subtilis* ΔyqjG-IspoIIIJ, first a fragment comprising the ribosome binding site, start codon and the 5' region of the spoIIIJ gene, but not the spoIIIJ promoter(s), was amplified with the primers spoIIIJ-3 (5'-GGA ATT CTA GAG TGT AAA GAT TAA TTA TAG GAG GAA ATG TTG-3'; SEQ ID NO:7) and spoIIIJ-2. The amplified fragment was cleaved with EcoRI and BamHI, and ligated into the corresponding sites of pMutin2, resulting in pMutin-IspoIIIJ. Finally, *B. subtilis* ΔyqjG-IspoIIIJ was obtained by Campbell-type integration of pMutin-IspoIIIJ into the spoIIIJ gene of *B. subtilis* yqjG-Tc, in such a way that the spoIIIJ gene and the downstream jag gene were placed under the control of the IPTG-dependent Pspac promoter, whereas the spoVG-lacZ reporter gene of pMutin2 was placed under the transcriptional control of the spoIIIJ promoter region (See, FIG. 2).

*B. subtilis* ΔyqjG-IspoIIIJ containing a xylose-inducible secDF-Myc gene was obtained by transformation of *B. subtilis* ΔyqjG-IspoIIIJ with chromosomal DNA of the xSecDF-Myc strain (Bolhuis et al., 1998). All constructed strains were selected on plates with the proper antibiotics, and checked by PCR analyses for correct integration of plasmids into the chromosome.

EXAMPLE 3

Growth and Maintenance of IPTG-Dependent *B. subtilis* ΔyqjG-IspoIIIJ Strains

The IPTG-dependent strain *B. subtilis* ΔyqjG-IspoIIIJ, and derivatives thereof, were grown in media containing 500 nM IPTG, Em (1 μg/ml) and Tc (6 μ/ml). It should be noted that in the absence of IPTG, such strains sometimes start to grow again after a lag period. This is probably due to the occurrence of a point mutation in the Pspac promoter, causing constitutive expression of the downstream genes (Prágai and Harwood, J. Bacteriol., 182:6819-6823 [2000]). To avoid this potential problem, prior to each experiment, individual colonies were replica-plated on plates without IPTG and colonies displaying no growth on the latter plates were used for SpoIIIJ/YqjG-depletion experiments. To this purpose, *B. subtilis* ΔyqjG-IspoIIIJ was grown overnight in TY medium supplemented with 500 nM IPTG, Em (1 μ/ml) and Tc (6 μg/ml). Cells were washed in fresh TY medium without IPTG and diluted 1:20 in fresh TY medium without, or with limiting concentrations (50 nM) of IPTG. After 3 hours of growth, cells were harvested. ΔyqjG-IspoIIIJ strains stop growing after about 2-3 hours in the absence of IPTG (See, FIG. 3, Panel A).

EXAMPLE 4

Sporulation and Growth of *Bacillus*

In this Example, results obtained regarding growth and sporulation of *B. subtilis* are described.

YqjG is Not Required for Sporulation

As indicated above, a yqjG disruption strain was constructed with the integration vector pMutin2 (See, FIG. 2). The fact that *B. subtilis* ΔyqjG could be obtained showed that YqjG, like SpoIIIJ, is not essential for growth (See, FIG. 3, Panel A). Notably, disruption of the yqjG gene did not detectably affect sporulation, while a ΔspoIIIJ control strain constructed with pMutin2 was unable to develop viable spores (data not shown). Thus, YqjG has no essential function in the sporulation process, in contrast to SpoIIIJ.

The Presence of Either SpoIIIJ or YqjG is Required for Growth of *B. subtilis*

To determine whether the combined activities of SpoIIIJ and YqjG are required for the viability of *B. subtilis* cells, a conditional (IPTG-dependent) yqjG-spoIIIJ double mutant strain was constructed in two steps. First, the largest part of the yqjG gene was replaced with a tetracycline resistance marker via double cross-over recombination. Second, the spoIIIJ gene of the latter strain was placed under the control of the isopropyl-β-D-thiogalacto-pyranoside (IPTG)-inducible Pspac promoter, present on pMutin2. This was achieved by single cross-over of pMutin2 into the spoIIIJ region of the chromosome. (See, FIG. 2). Notably, the resulting *B. subtilis* ΔyqjG-IspoIIIJ strain could be obtained only in the presence of IPTG, indicating that at least the spoIIIJ gene had to be transcribed for the growth of this strain. In fact, as indicated in FIG. 3, Panel A, about 500 nM IPTG was required for this strain to display unimpaired growth on TY agar plates at 37° C. Upon dilution in fresh TY medium without IPTG, *B. subtilis* ΔyqjG-IspoIIIJ stopped growing after 2-3 hours of incubation (See, FIG. 3, Panel B). Similar to the IPTG-dependent growth of this strain on TY plates, the presence of 500 nM IPTG was required to support wild-type growth of *B. subtilis* ΔyqjG-IspoIIIJ in liquid TY medium at 37° C. In contrast, growth of *B. subtilis* ΔyqjG-IspoIIIJ in the presence of 50 nM IPTG was significantly reduced as compared to that of the parental strain 168, indicating that SpoIIIJ was synthesized at limiting levels. Importantly, growth of *B. subtilis* ΔyqjG-IspoIIIJ in the absence of IPTG could be restored by the ectopic expression of the spoIIIJ gene, showing that the growth inhibition of this strain is due to SpoIIIJ limitation, and not to polar effects on the expression of the downstream-located jag gene. Together with the observation that spoIIIJ and yqjG single mutants are viable, these findings show that the presence of either SpoIIIJ or YqjG is required for growth of *B. subtilis*. Notably, the IPTG-dependence of *B. subtilis* ΔyqjG-IspoIIIJ was strongly increased at 15° C. (See, FIG. 3, Panel A). As protein transport via the Sec pathways of *B. subtilis* and *E. coli* is intrinsically cold-sensitive (Bolhuis et al., [1998], supra; Pogliano and Beckwith, supra; and van Wely et al., [1999], supra), the observed temperature effect suggests that SpoIIIJ and YqjG have a role in Sec-dependent protein transport.

Maximal spoIIIJ and yqjG Transcription in the Exponential Growth Phase

Previous studies showed that the spoIIIJ gene is transcribed during the exponential growth phase and that this transcription is shut down at about the onset of sporulation (See, Errington et al., supra). To determine whether the transcription of the yqjG gene is regulated in a similar manner, the transcriptional yqjGlacZ and spoIIIJ-lacZ gene fusions that are present in *B. subtilis* ΔyqjG and ΔspoIIIJ, respectively (See, FIG. 2) were used during the development of the present invention. Both strains were grown in TY medium, minimal medium, or sporulation medium, and samples withdrawn at hourly intervals were assayed for β-galactosidase activity. The results showed that, irrespective of the growth medium, the β-galactosidase levels in both strains reached a maximum in the exponential phase (See, FIG. 3, Panel C—only the results obtained with cells grown in TY medium are indicated). The β-galactosidase levels were strongly decreased upon the transition (t=0) into the post-exponential growth phase. As the transcription profiles of the yqjG-lacZ gene fusion were very similar to those of the spoIIIJ-lacZ fusion under all conditions tested, it seems highly unlikely that the lack of effect of a yqjG mutation on sporulation is due to differences in the transcription of these genes.

EXAMPLE 5

Protein Secretion

In this Example, results of experiments to assess protein secretion by *B. subtilis* and various mutant strains are described.

SpoIIIJ and YqjG are Required for Efficient Protein Secretion

To evaluate the importance of YqjG and SpoIIIJ function for protein secretion, *B. subtilis* ΔyqlG, ΔspoIIIJ, and ΔyqjG-IspoIIIJ, as well as the parental strain 168, were transformed with plasmid pLip2031 for the secretion of the *B. subtilis* lipase LipA (Dartois et al., supra), pPSPPhoA5 for the secretion of the alkaline phosphatases PhoA of *E. coli* fused to the prepro-region of the lipase gene from *Staphylococcus hyicus* (Bolhuis et al., [1999b], supra), or pKTH10 for the secretion of the a-amylase AmyQ (Palva, supra). As no secretion defects were detectable in the single mutant strains (data not shown), attention was focused on the ΔyqjG-IspoIIIJ double mutant. In order to deplete *B. subtilis* ΔyqjG-IspoIIIJ of SpoIIIJ, this strain was grown for three hours in TY medium without IPTG, as described above. As a control, TY medium with 50 nM IPTG (limiting amounts of SpoIIIJ), or 500 nM IPTG (full induction of SpoIIIJ) was used (See, FIG. 3, Panels A and B). Next, the secretion of LipA, PhoA and AmyQ was analyzed by Western blotting, as described above. As shown in FIG. 4, Panel A (lower panels), the levels of LipA, PhoA and AmyQ in the medium of SpoIIIJ-depleted cells of *B. subtilis* ΔyqjG-IspoIIIJ (no IPTG) were significantly reduced compared to those in the media of the fully induced double mutant (500 nM IPTG), or the parental strain 168. Moreover, SpoIIIJ-depleted double mutant cells containing pPSPPhoA5 or pKTH10 also contained significantly decreased levels of mature PhoA or AmyQ, respectively (See, FIG. 4, Panel A). In contrast, the cellular levels of mature LipA, and the precursor forms of LipA and AmyQ were not affected by SpoIIIJ depletion in the absence of YqjG (See, FIG. 4, Panel A, upper panels). Interestingly, the levels of LipA and PhoA in the media of ΔyqjG-IspoIIIJ strains that were fully induced with IPTG (500 nM), were higher than those in the media of the parental control strains. The latter finding suggests that overexpression of the spoIIIJ gene can result in improved protein secretion in *B. subtilis*.

To investigate the nature of the secretion defect of *B. subtilis* ΔyqjG-IspoIIIJ, further experiments were performed with AmyQ and an AmyQ variant (AmyQ-PSBT) as described by Bolhuis et al. (Bolhuis et al., [1998], supra). As shown by pulse-chase labeling experiments, at early chase times (0 and 1 min of chase), the pre-AmyQ synthesis and processing in cells of *B. subtilis* ΔyqjG-IspoIIIJ depleted of SpoIIIJ (no IPTG) was not significantly different from that observed in cells of this strain in which SpoIIIJ was fully induced (500 nM IPTG; See, FIG. 4, Panel B), or the parental strain 168 (data not shown). However, in particular after 5 min of chase, significantly reduced amounts of mature AmyQ were detectable in the ΔyqjG-IspoIIIJ cells depleted of SpoIIIJ. This suggests that these cells have a defect in post-translocational protein folding rather than a defect in protein translocation. To verify that SpoIIIJ-depleted cells lacking YqjG have no translocation defect, experiments were performed with AmyQ-PSBT, which contains a carboxyl-terminal biotin accepting domain (PSBT) of a transcarboxylase from *Propionibacterium shermannii* (Tjalsma et al., [1998], supra). The rationale of this experiment is that pre-AmyQ-PSBT can only be biotinylated by the cytoplasmic biotin ligase when the PSBT domain folds into its native three-dimensional structure prior to translocation. Consequently, biotinylation of pre-AmyQ-PSBT occurs at significantly increased levels when pre-AmyQ-PSBT translocation is slowed-down, for example by the disruption of the secDF gene (Bolhuis et al [1998], supra). As shown in FIG. 4, Panel C, SpoIIIJ-depleted cells lacking YqjG did not accumulate increased amounts of biotinylated pre-AmyQ-PSBT as compared to cells in which SpoIIIJ synthesis was induced with IPTG, or the parental strain 168. In contrast, *B. subtilis* cells with a disrupted secDF gene (positive control) accumulated strongly increased amounts of biotinylated AmyQ-PSBT (See, FIG. 4, Panel C). Notably, the biotinylated AmyQ-PSBT in the ΔsecDF cells was found to be present both in the precursor and mature forms. Taken together, these observations support the view that the translocation of pre-AmyQ is not affected in SpoIIIJ-depleted cells lacking YqjG. Instead, SpoIIIJ and YqjG appear to be very important for the post-translocational folding stages in protein secretion.

Figure 5B:
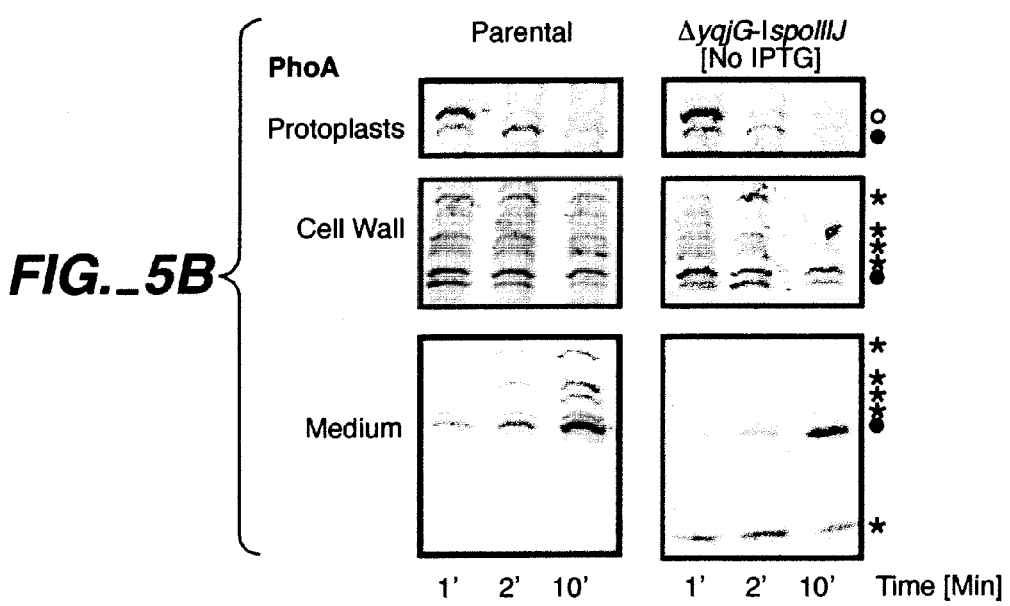
Figure 5C:
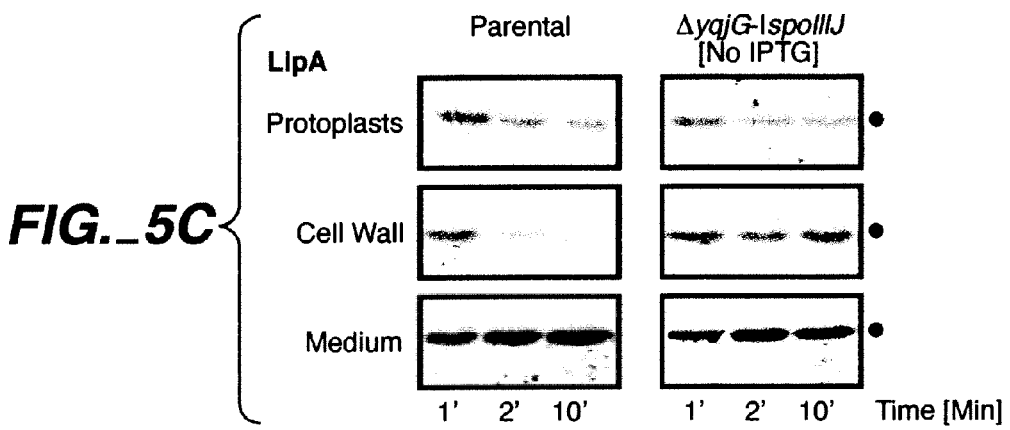

SpoIIIJ and YqjG are Required for Efficient Post-Translocational Folding and Release of Secretory Proteins While previous data show that the depletion of YqjG and SpoIIIJ affects a post-translocational step in protein secretion, it does not show whether AmyQ, PhoA and LipA are degraded before or after release into the medium of *B. subtilis*. Therefore, a pulse-chase experiment followed by protein localization was performed as described above, in order to identify the site at which secretory proteins are subject to degradation. As shown in FIG. 5, Panel A, the pre-AmyQ synthesis and processing (upper panel) in cells of *B. subtilis* ΔyqjG-IspoIIIJ depleted of SpoIIIJ (no IPTG), and release of AmyQ into the cell wall (middle panel) were not significantly different from that observed in cells of the parental strain. However, the amount of AmyQ that was released into the medium after 10 min of chase (lower panel), was about threefold reduced in the ΔyqjG-IspoIIIJ cells depleted of SpoIIIJ. Furthermore, a specific AmyQ degradation product was only released into the medium of ΔyqjG-IspoIIIJ cells depleted of SpoIIIJ. Similarly, the pre-pro-PhoA synthesis and processing (See, FIG. 5, Panel B, upper panel) in cells of *B. subtilis* ΔyqjG-IspoIIIJ depleted of SpoIIIJ (no IPTG), and release of AmyQ into the cell wall (middle panel) were not significantly different from that observed in cells of the parental strain. It was noted that pro-PhoA is extremely unstable, as at least four degradation products of pro-PhoA were detected in the cell wall and medium fractions (middle and lower panels). However, the levels of these degradation products were significantly reduced in the cell wall of *B. subtilis* ΔyqjG-IspoIIIJ depleted of SpoIIIJ. Furthermore, the release of these pro-PhoA forms and mature PhoA into the medium of *B. subtilis* ΔyqjG-IspoIIIJ depleted of SpoIIIJ was found to be reduced compared to the parental strain (about 2-fold; lower panel). Finally, a specific PhoA degradation product was only released into the medium of ΔyqjG-IspoIIIJ cells depleted of SpoIIIJ (lower panel). Similarly, the LipA synthesis and processing (See, FIG. 5, Panel B, upper panel) in cells of *B. subtilis* ΔyqjG-IspoIIIJ depleted of SpoIIIJ (no IPTG), and release of AmyQ into the cell wall (middle panel) was not significantly different from that observed in cells of the parental strain. However, the release of LipA into the medium of ΔyqjG-IspoIIIJ cells depleted of SpoIIIJ was slightly impaired compared to the release of LipA from the cell wall of the parental strain (middle and lower panels). It was noted that under these conditions the LipA secretion defect in cells of *B. subtilis* ΔyqjG-IspoIIIJ depleted of SpoIIIJ seems to be mild compared to the defect observed in rich medium (See, FIG. 4, Panel A). Together, these data show that mature AmyQ and (pro-)PhoA are significantly less stable in the membrane-cell wall interface of *B. subtilis* ΔyqjG-IspoIIIJ depleted of SpoIIIJ. The fact that degradation products are already released into the medium at t=1', indicates that degradation occurs soon after the precursors have left the translocation channel. Thus, these observation indicate that the secretion defects in *B. subtilis* cells depleted of YqjG and SpoIIIJ relate to impaired folding of secretory proteins in the membrane-cell wall interface and subsequent degradation prior to release of the secretory protein into the medium.

EXAMPLE 6

Membrane Protein Stability and Topology

In this Example, results from experiments conducted to assess membrane protein stability and topology are described.

SpoIIIJ and YqjG are of Minor Importance for Membrane Protein Stability and Topology As shown by Samuelson et al. (Samuelson et al., supra), the YidC protein of *E. coil* is very important for the correct insertion of various proteins into the inner membrane, but not the export and processing of Sec-dependent pre-proteins. To investigate whether the SpoIIIJ and YqjG functions could be required for membrane protein biogenesis in *B. subtilis*, the cellular levels of the BdbB, BdbC, FtsH, PrsA, SecDF-Myc, SipS, and SPase II proteins in the ΔyqjG-IspoIIIJ strain were monitored by Western blotting. These proteins were primarily selected because they have different membrane topologies and different numbers of transmembrane segments (See, FIG. 6; results are not shown for BdbB/C and SPase II, which have four transmembrane segments and an Nin-Cin topology). Furthermore, these proteins, which are known to be involved in protein secretion by *B. subtilis* (Tjalsma et al., [2000a], supra), were selected to investigate whether the secretion defects of SpoIIIJ-depleted cells lacking YqjG might be indirectly caused by the impaired membrane biogenesis of secretion machinery components. Interestingly, the levels of SecDF-Myc, SipS, and PrsA were not detectably affected in SpoIIIJ-depleted cells lacking YqjG that were grown at 37° C. (See, FIG. 6), or 15° C. (data not shown). Similarly, the cellular amounts of BdbB, BdbC and SPase II remained unchanged (data not shown). In fact, FtsH was the only protein involved in protein secretion (Deuerling et al., Mol. Microbiol. 23:921-933 [1997]) that was (mildly) affected upon SpoIIIJ depletion in the absence of YqjG. As shown in FIG. 6, low amounts of FtsH degradation products (lower panel) accumulated in ΔyqjG-IspoIIIJ cells depleted of SpoIIIJ.

The Oxa1p protein of yeast mitochondria was previously shown to be required for the correct assembly of cytochrome c oxidase complexes (Bonnefoy et al., Proc. Natl. Acad. Sci. USA 91:11978-11982 [1994]; and Altemura et al., FEBS Lett., 382:111-115 [1996]), and the specific export of the amino- and carboxyl-termini of pre-Cox II from the mitochondrial matrix to the intermembrane space (Hell et al., [1997], supra; Hell et al., [1998], supra; and He and Fox, Mol. Biol. Cell., 8:1449-1460 [1997]). Therefore, a possible role of SpoIIIJ and YqjG in the biogenesis of the transmembrane lipoproteins CtaC and QoxA, which are orthologues of Cox II (Bengtsson et al., J. Bacteriol., 181:685-688 [1999]), was investigated during the development of the present invention. Indeed, the results showed that, upon SpoIIIJ depletion of cells lacking YqjG, the cellular levels of CtaC were slightly reduced, while a specific CtaC degradation product accumulated concomitantly (See, FIG. 6). However, as also shown in FIG. 6, under the same conditions, the cellular level and stability of QoxA were not detectably affected.

Previous studies by de Gier et al (de Gier et al., FEBS Lett., 399:307-309 [1996]) have shown that impaired membrane protein insertion does not necessarily affect the total cellular levels of membrane proteins. To determine whether membrane proteins were properly inserted in SpoIIIJ-depleted cells lacking YqjG, the membrane topology of SecDF-Myc, SipS, PrsA, FtsH, CtaC and QoxA was assessed by protoplasting and subsequent protease mapping assays, as described in Example 1. As shown in FIG. 7, the protease accessibility of none of the tested membrane proteins, was detectably affected in ΔyqjG-IspoIIIJ cells upon SpoIIIJ depletion. The cytoplasmic protein GroEL was not degraded by extracellular trypsin, indicating that lysis of protoplasts did not occur during the assay. It should be noted that the degradation product of FtsH, which accumulates in ΔyqjG-IspoIIIJ cells depleted of SpoIIIJ (See, FIG. 6), was also detectable in the parental strain upon protoplasting. Also, the degradation product of CtaC, which accumulates in ΔyqjG-IspoIIIJ cells depleted of SpoIIIJ (See, FIG. 6), was not detectable upon protoplasting of these cells.

To examine the kinetics of membrane protein insertion, a pulse-chase/protease mapping experiment was performed with cells of the parental *B. subtilis* 168 strain and ΔyqjGIspoIIIJ cells upon SpoIIIJ-depletion. As shown in FIG. 8, the protease accessibility of SipS, PrsA and QoxA was not detectably affected in ΔyqjG-IspoIIIJ cells upon SpoIIIJ depletion after a 1-min chase. GroEL was not degraded by extracellular trypsin, indicating that no lysis of protoplasts occurred during this assay. Consistent with the lack of effect on the insertion of PrsA in the membrane, the processing of pre-PrsA by SPase II, as verified by pulse-chase labeling, was not affected in ΔyqjG-IspoIIIJ cells upon SpoIIIJ-depletion (data not shown). Unfortunately, neither SecDF-Myc, CtaC, nor FtsH were tested in pulse-chase experiments as it was not possible to immunoprecipitate these proteins, most likely due to rapid degradation by endogenous *B. subtilis* proteases.

Taken together, these findings show that the stability of some membrane proteins is affected in cells with limiting amounts of SpoIIIJ and YqjG. However, the stability, topology and insertion kinetics of other membrane proteins and membrane-associated components of the *Bacillus* secretion machinery is not significantly affected under those conditions. Thus, it is contemplated that the defect in the secretion of AmyQ, LipA and PhoA secretion is not caused by impaired membrane assembly of individual protein secretion machinery components.

From the above, it is clear that the present invention provides methods and compositions for the modulation of Sec-dependent protein secretion. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, protein expression, and/or related fields are intended to be within the scope of the present invention.

We claim:

1. A method of modulating Sec-dependent protein secretion comprising the steps of:
   a) introducing a spoIIIJ gene linked to an inducible promoter into a *Bacillus* cell; and
   b) modulating the expression of the spoIIIJ gene by varying the level of induction of the inducible promoter.

2. The method of claim 1, wherein the inducible promoter is the Pspac promoter.

3. A purified DNA molecule comprising an inducible promoter operatively linked to the spoIIIJ gene.

4. A method of modulating the secretion of a protein of interest, comprising the steps of:
   a) forming a first DNA molecule encoding a chimeric protein comprising a Sec-dependent secretion signal peptide;
   b) forming a second DNA molecule encoding an inducible promoter operably linked to the spoIIIJ gene;
   c) transforming a *Bacillus* host cell with the DNA molecule of steps a and b; and
   d) growing said host cell under conditions wherein the protein of interest is expressed at the desired level.

5. The method of claim 4, wherein said host cell is grown under conditions wherein the inducible promoter is induced.

6. A method of modulating the secretion of a protein of interest, comprising the steps of:
   a) forming a first DNA molecule encoding a chimeric protein comprising a Sec-dependent secretion signal peptide;
   b) forming a second DNA molecule encoding an inducible promoter operably linked to the yqjG gene;
   c) transforming a *Bacillus* host cell with the DNA molecule of steps a and b; and
   d) growing said host cell under conditions wherein the protein of interest is expressed at the desired level.

7. The method of claim 6, wherein said host cell is grown under conditions wherein the inducible promoter is induced.

8. A method of modulating Sec-dependent protein secretion comprising the steps of:
   a) providing a *Bacillus* cell comprising spoIIIJ and yqjG genes linked to an inducible promoter; and
   b) modulating the expression of the spoIIIJ and yqjG genes by varying the level of induction of said promoter.

9. The method of claim 8, wherein the promoter is the Pspac promoter.

* * * * *